(12) United States Patent
Downing et al.

(10) Patent No.: US 8,858,533 B2
(45) Date of Patent: Oct. 14, 2014

(54) METHODS AND SYSTEMS FOR PROVIDING FLUID COMMUNICATION WITH A GASTROSTOMY TUBE

(75) Inventors: Anthony Downing, Ayer, MA (US);
James Wilkie, Melrose, MA (US);
Ronald Court, Pelham, NH (US);
Steven Jacques, Westford, MA (US);
Michael W. Gauderer, Greenville, SC (US)

(73) Assignee: C. R. Bard, Inc., Murray Hill, NJ (US)

( * ) Notice: Subject to any disclaimer, the term of this patent is extended or adjusted under 35 U.S.C. 154(b) by 353 days.

(21) Appl. No.: 11/629,724

(22) PCT Filed: Jun. 29, 2005

(86) PCT No.: PCT/US2005/023297
§ 371 (c)(1),
(2), (4) Date: Aug. 3, 2007

(87) PCT Pub. No.: WO2006/004943
PCT Pub. Date: Jan. 12, 2006

(65) Prior Publication Data
US 2007/0276356 A1    Nov. 29, 2007

Related U.S. Application Data

(60) Provisional application No. 60/583,703, filed on Jun. 29, 2004.

(51) Int. Cl.
| | |
|---|---|
| *A61M 25/16* | (2006.01) |
| *A61M 25/18* | (2006.01) |
| *A61M 39/02* | (2006.01) |
| *A61M 39/24* | (2006.01) |
| *A61M 39/12* | (2006.01) |
| *A61M 39/10* | (2006.01) |

(52) U.S. Cl.
CPC ....... *A61M 39/24* (2013.01); *A61M 2039/2426* (2013.01); *A61M 2039/1077* (2013.01); *A61M 2039/242* (2013.01); *A61M 39/12* (2013.01)
USPC ............................ 604/539; 604/910; 604/537

(58) Field of Classification Search
CPC ............. A61M 2025/0233; A61M 2210/1053; A61M 39/10; A61M 2039/0255; A61J 15/0015; A61J 15/0034; A61J 15/0038; A61J 15/0057; A61J 15/0061
USPC .................. 604/174, 164.04, 164.07, 165.01, 604/167.01–167.04, 175, 537, 539, 910, 604/533–535
See application file for complete search history.

(56) References Cited

U.S. PATENT DOCUMENTS

| | | |
|---|---|---|
| 1,719,428 A | 7/1929 | Friedman |
| 2,230,226 A | 2/1941 | Auzin |

(Continued)

FOREIGN PATENT DOCUMENTS

| | | |
|---|---|---|
| EP | 0930083 A2 | 7/1999 |
| EP | 2060293 A1 | 5/2009 |

(Continued)

OTHER PUBLICATIONS

International Search Report dated May 26, 2006 from related International Application No. PCT/US05/23297.

(Continued)

*Primary Examiner* — Rebecca E Eisenberg
(74) *Attorney, Agent, or Firm* — Rutan & Tucker, LLP

(57) ABSTRACT

A low profile adaptor is disclosed to reduce the length of a gastrostomy tube that has been inserted by means of conventional endoscopic procedures or with a replacement feeding tube inserted into the patient's stomach. The gastrostomy tube is cut to the appropriate length by the physician. The adaptor comprises a stem which is inserted into the open end of the gastrostomy tube. The valve assembly contains a seal that functions as a one-way valve to prevent reflux of gastric contents but permits the introduction of feeding solution into the feeding tube. A lock and key mechanism is incorporated into the hub of the gastrostomy tube to prevent disconnection of the feeding tube. A cover is placed over the opening of the adapter to prevent contamination of the lumen of the gastrostomy tube.

24 Claims, 19 Drawing Sheets

(56) References Cited

U.S. PATENT DOCUMENTS

| | | |
|---|---|---|
| 3,111,930 A | 11/1963 | Zipper |
| 3,241,514 A | 3/1966 | Grimland |
| 3,397,699 A | 8/1968 | Kohl |
| 3,543,759 A | 12/1970 | McWhorter |
| 3,731,691 A | 5/1973 | Chen |
| 3,915,171 A | 10/1975 | Shermeta |
| 4,016,885 A | 4/1977 | Bruner |
| 4,043,338 A | 8/1977 | Homm et al. |
| 4,134,407 A | 1/1979 | Elam |
| 4,177,815 A | 12/1979 | Patel |
| 4,227,293 A | 10/1980 | Taylor |
| 4,245,639 A | 1/1981 | La Rosa |
| 4,366,708 A | 1/1983 | Warihashi |
| 4,370,982 A | 2/1983 | Reilly |
| 4,398,542 A | 8/1983 | Cunningham et al. |
| 4,535,757 A | 8/1985 | Webster, Jr. |
| 4,583,917 A | 4/1986 | Shah |
| 4,592,747 A | 6/1986 | Pool |
| 4,606,347 A | 8/1986 | Fogarty et al. |
| 4,608,965 A | 9/1986 | Anspach, Jr. et al. |
| 4,617,015 A | 10/1986 | Foltz |
| 4,666,433 A | 5/1987 | Parks |
| 4,685,901 A | 8/1987 | Parks |
| 4,701,163 A | 10/1987 | Parks |
| 4,729,706 A | 3/1988 | Peterson et al. |
| 4,744,788 A | 5/1988 | Mercer, Jr. |
| 4,798,592 A | 1/1989 | Parks |
| 4,863,438 A | 9/1989 | Gauderer et al. |
| 4,872,483 A | 10/1989 | Shah |
| 4,929,236 A * | 5/1990 | Sampson ............... 604/175 |
| 4,944,732 A | 7/1990 | Russo |
| 4,994,034 A | 2/1991 | Botich et al. |
| 5,007,900 A | 4/1991 | Picha et al. |
| 5,071,405 A | 12/1991 | Piontek et al. |
| 5,111,310 A | 5/1992 | Parker et al. |
| 5,112,310 A | 5/1992 | Grobe |
| 5,163,949 A | 11/1992 | Bonutti |
| 5,178,423 A * | 1/1993 | Combeau ............... 285/247 |
| 5,203,773 A | 4/1993 | Green |
| 5,218,970 A | 6/1993 | Turnbull et al. |
| 5,234,454 A | 8/1993 | Bangs |
| 5,248,302 A | 9/1993 | Patrick et al. |
| 5,255,670 A | 10/1993 | Lomholt |
| 5,273,529 A | 12/1993 | Idowu |
| 5,275,610 A | 1/1994 | Eberbach |
| 5,279,564 A | 1/1994 | Taylor |
| 5,308,325 A | 5/1994 | Quinn et al. |
| 5,309,906 A | 5/1994 | LaBombard |
| 5,324,262 A | 6/1994 | Fischell et al. |
| 5,342,321 A | 8/1994 | Potter |
| 5,365,967 A | 11/1994 | Moore |
| 5,399,173 A | 3/1995 | Parks et al. |
| 5,403,290 A | 4/1995 | Noble |
| 5,411,491 A | 5/1995 | Goldhardt et al. |
| 5,429,598 A | 7/1995 | Waxman et al. |
| 5,429,605 A | 7/1995 | Richling et al. |
| 5,439,444 A | 8/1995 | Andersen et al. |
| 5,458,572 A | 10/1995 | Campbell et al. |
| 5,458,583 A | 10/1995 | McNeely et al. |
| 5,462,528 A | 10/1995 | Roewer |
| 5,462,561 A | 10/1995 | Voda |
| 5,470,314 A | 11/1995 | Walinsky |
| 5,514,112 A | 5/1996 | Chu et al. |
| 5,522,961 A | 6/1996 | Leonhardt |
| 5,527,280 A | 6/1996 | Goelz |
| 5,549,657 A | 8/1996 | Stern et al. |
| D373,418 S | 9/1996 | Szpak |
| 5,556,385 A | 9/1996 | Andersen |
| 5,681,280 A | 10/1997 | Rusk et al. |
| 5,720,734 A | 2/1998 | Copenhaver et al. |
| 5,749,852 A | 5/1998 | Schwab et al. |
| 5,836,924 A | 11/1998 | Kelliher et al. |
| 5,860,960 A | 1/1999 | Quinn |
| 5,910,128 A | 6/1999 | Quinn |
| 5,935,107 A | 8/1999 | Taylor et al. |
| 5,941,855 A | 8/1999 | Picha et al. |
| 5,993,473 A | 11/1999 | Chan et al. |
| 5,997,503 A | 12/1999 | Willis et al. |
| 5,997,546 A | 12/1999 | Foster et al. |
| 6,033,379 A | 3/2000 | Barra et al. |
| 6,045,536 A | 4/2000 | Meier et al. |
| 6,050,987 A | 4/2000 | Rosenbaum |
| 6,066,112 A | 5/2000 | Quinn |
| 6,066,155 A | 5/2000 | Amann et al. |
| 6,077,243 A | 6/2000 | Quinn |
| 6,113,572 A | 9/2000 | Gailey et al. |
| 6,113,579 A | 9/2000 | Eidenschink et al. |
| 6,149,575 A | 11/2000 | Leonhardt |
| 6,186,985 B1 | 2/2001 | Snow |
| 6,221,042 B1 | 4/2001 | Adams |
| 6,228,063 B1 | 5/2001 | Aboul-Hosn |
| 6,264,631 B1 | 7/2001 | Willis et al. |
| 6,315,789 B1 | 11/2001 | Cragg |
| 6,319,244 B2 | 11/2001 | Suresh et al. |
| 6,432,080 B2 | 8/2002 | Pederson, Jr. et al. |
| 6,506,179 B1 | 1/2003 | Tiefenthal et al. |
| 6,530,898 B1 | 3/2003 | Nimkar et al. |
| 6,565,536 B1 | 5/2003 | Sohn |
| 6,582,395 B1 | 6/2003 | Burkett et al. |
| 6,595,971 B1 | 7/2003 | von Dyck et al. |
| 6,641,177 B1 * | 11/2003 | Pinciaro ............... 285/242 |
| 6,666,853 B2 | 12/2003 | Chu et al. |
| 6,669,681 B2 * | 12/2003 | Dudar et al. ............... 604/533 |
| 6,702,336 B1 * | 3/2004 | Chelchowski et al. ....... 285/343 |
| 6,705,320 B1 | 3/2004 | Anderson |
| 6,732,734 B2 | 5/2004 | Ogushi et al. |
| D490,890 S | 6/2004 | Li |
| 6,858,019 B2 | 2/2005 | McGuckin, Jr. et al. |
| 6,878,130 B2 | 4/2005 | Fournie et al. |
| 6,896,665 B2 | 5/2005 | Picha et al. |
| 6,916,307 B2 | 7/2005 | Willis et al. |
| 6,960,222 B2 | 11/2005 | Vo et al. |
| 6,976,980 B2 * | 12/2005 | Brenner et al. ............... 604/535 |
| 6,997,909 B2 | 2/2006 | Goldberg |
| 7,008,438 B2 | 3/2006 | O'Brien |
| 7,008,441 B2 | 3/2006 | Zucker |
| 7,041,083 B2 | 5/2006 | Chu et al. |
| 7,060,050 B2 | 6/2006 | Kliem et al. |
| 7,070,587 B2 | 7/2006 | Meier |
| 7,124,489 B2 | 10/2006 | Triebes et al. |
| 7,186,238 B2 | 3/2007 | Elbert et al. |
| 7,220,243 B2 | 5/2007 | Bonnette et al. |
| 7,341,284 B2 * | 3/2008 | Mittersteiner et al. ........ 285/247 |
| 7,534,224 B2 | 5/2009 | Triebes et al. |
| 7,547,303 B2 | 6/2009 | DeLegge |
| 7,582,072 B2 | 9/2009 | McMichael |
| 7,621,903 B2 | 11/2009 | DeLegge |
| 7,625,361 B2 | 12/2009 | Suzuki et al. |
| 7,628,775 B2 | 12/2009 | Adams et al. |
| 7,819,840 B2 | 10/2010 | Burnside et al. |
| 8,206,347 B2 | 6/2012 | Burnside et al. |
| 8,226,632 B2 * | 7/2012 | Zawacki et al. ............... 604/533 |
| 8,715,244 B2 | 5/2014 | Prechtel et al. |
| 2002/0093199 A1 | 7/2002 | Le |
| 2003/0055454 A1 | 3/2003 | Zucker |
| 2003/0088213 A1 | 5/2003 | Schweikert et al. |
| 2003/0120260 A1 * | 6/2003 | Chu et al. ............... 604/533 |
| 2003/0212385 A1 | 11/2003 | Brenner et al. |
| 2003/0225376 A1 | 12/2003 | Fournie et al. |
| 2004/0041399 A1 | 3/2004 | Chelchowski et al. |
| 2004/0087984 A1 | 5/2004 | Kupiecki et al. |
| 2004/0103518 A1 | 6/2004 | Triebes et al. |
| 2004/0106899 A1 | 6/2004 | McMichael et al. |
| 2004/0106901 A1 | 6/2004 | Letson et al. |
| 2004/0147874 A1 | 7/2004 | Kliem et al. |
| 2004/0181235 A1 | 9/2004 | Daignault et al. |
| 2005/0038381 A1 | 2/2005 | McMichael |
| 2005/0200122 A1 | 9/2005 | Mittersteiner et al. |
| 2005/0267415 A1 | 12/2005 | Jacques |
| 2006/0206095 A1 * | 9/2006 | Chu et al. ............... 604/539 |
| 2006/0270989 A1 | 11/2006 | McMichael et al. |
| 2006/0276746 A1 | 12/2006 | Burnside et al. |
| 2007/0021771 A1 | 1/2007 | Oepen et al. |
| 2007/0088259 A1 | 4/2007 | Chu et al. |

(56) References Cited

U.S. PATENT DOCUMENTS

| | | | |
|---|---|---|---|
| 2007/0123842 | A1 | 5/2007 | Teague et al. |
| 2007/0244426 | A1 | 10/2007 | Hart et al. |
| 2007/0255209 | A1 | 11/2007 | Crooms et al. |
| 2008/0058730 | A1 | 3/2008 | Melsheimer |
| 2008/0188897 | A1 | 8/2008 | Krebs et al. |
| 2009/0112183 | A1 | 4/2009 | Jacques |
| 2009/0318873 | A1 | 12/2009 | Bailey |
| 2010/0004601 | A1 | 1/2010 | Deckard |
| 2010/0010448 | A1 | 1/2010 | Deckard |
| 2010/0057013 | A1 | 3/2010 | Harada |
| 2010/0185155 | A1 | 7/2010 | McMichael et al. |
| 2010/0312192 | A1 | 12/2010 | Fitzgerald et al. |
| 2011/0152762 | A1 | 6/2011 | Hershey et al. |
| 2011/0196341 | A1 | 8/2011 | Howell |
| 2012/0053485 | A1 | 3/2012 | Bloom |
| 2012/0238959 | A1 | 9/2012 | Thorne et al. |
| 2012/0245519 | A1 | 9/2012 | Rotella et al. |

FOREIGN PATENT DOCUMENTS

| | | |
|---|---|---|
| EP | 2451512 A1 | 5/2012 |
| JP | 2000-515797 T | 11/2000 |
| JP | 4988725 B2 | 8/2012 |
| JP | 2012192182 A | 10/2012 |
| JP | 5184512 | 4/2013 |
| JP | 2013-518697 A | 5/2013 |
| WO | 9819730 A1 | 5/1998 |
| WO | 9852631 A1 | 11/1998 |
| WO | 02087492 A1 | 11/2002 |
| WO | 2004050009 A1 | 6/2004 |
| WO | 2007087254 A2 | 8/2007 |
| WO | 2009135141 A1 | 11/2009 |
| WO | 2011005847 A1 | 1/2011 |
| WO | 2011100310 A2 | 8/2011 |

OTHER PUBLICATIONS

JP 2007-519438 filed Jun. 29, 2005 Decision to Grant dated Sep. 4, 2012.
PCT/US11/24176 filed Feb. 9, 2011 International Preliminary Report on Patentability dated Oct. 11, 2012.
PCT/US11/24176 filed Feb. 9, 2011 International Search Report and Written Opinion dated Jul. 8, 2011.
PCT/US2006/022020 filed Jun. 6, 2006 International Preliminary Report on Patentability dated Dec. 6, 2007.
PCT/US2006/022020 filed Jun. 6, 2006 Search Report dated Jan. 25, 2007.
PCT/US2006/022020 filed Jun. 6, 2006 Written Opinion dated Jan. 25, 2007.
PCT/US2010/041192 filed Jul. 7, 2010 International Search Report dated Sep. 20, 2010.
PCT/US2010/041192 filed Jul. 7, 2010 Written Opinion dated Sep. 20, 2010.
U.S. Appl. No. 11/127,662, filed May 12, 2005 Advisory Action dated May 16, 2008.
U.S. Appl. No. 11/127,662, filed May 12, 2005 Final Office Action dated Mar. 5, 2008.
U.S. Appl. No. 11/127,662, filed May 12, 2005 Final Office Action dated Mar. 6, 2007.
U.S. Appl. No. 11/127,662, filed May 12, 2005 Non-Final Office Action dated Aug. 9, 2007.
U.S. Appl. No. 11/127,662, filed May 12, 2005 Non-Final Office Action dated Jul. 9, 2008.
U.S. Appl. No. 11/127,662, filed May 12, 2005 Non-Final Office Action dated Oct. 17, 2006.
U.S. Appl. No. 11/422,559, filed Jun. 6, 2006 Final Office Action dated Apr. 2, 2009.
U.S. Appl. No. 11/422,559, filed Jun. 6, 2006 Non-Final Office Action dated Aug. 8, 2008.
U.S. Appl. No. 11/422,559, filed Jun. 6, 2006 Non-Final Office Action dated Jan. 6, 2010.
U.S. Appl. No. 11/422,559, filed Jun. 6, 2006 Notice of Allowance dated Jun. 24, 2010.
U.S. Appl. No. 11/738,979, filed Apr. 23, 2007 Final Office Action dated Jan. 13, 2012.
U.S. Appl. No. 11/738,979, filed Apr. 23, 2007 Advisory Action dated Jun. 18, 2009.
U.S. Appl. No. 11/738,979, filed Apr. 23, 2007 Final Office Action dated Apr. 16, 2009.
U.S. Appl. No. 11/738,979, filed Apr. 23, 2007 Final Office Action dated Jan. 25, 2010.
U.S. Appl. No. 11/738,979, filed Apr. 23, 2007 Non-Final Office Action dated Nov. 24, 2008.
U.S. Appl. No. 11/738,979, filed Apr. 23, 2007 Non-Final Office Action dated Oct. 9, 2009.
U.S. Appl. No. 12/265,102, filed Nov. 5, 2008 Advisory Action dated Apr. 3, 2012.
U.S. Appl. No. 12/265,102, filed Nov. 5, 2008 Final Office Action dated Jan. 13, 2012.
U.S. Appl. No. 12/265,102, filed Nov. 5, 2008 Non-Final Office Action dated Dec. 18, 2012.
U.S. Appl. No. 12/265,102, filed Nov. 5, 2008 Non-Final Office Action dated Jul. 29, 2011.
U.S. Appl. No. 12/831,644, filed Jul. 7, 2010 Non-Final Office Action dated Mar. 30, 2012.
U.S. Appl. No. 12/902,987, filed Oct. 12, 2010 Final Office Action and Reasons for Allowance dated Dec. 22, 2011.
U.S. Appl. No. 12/902,987, filed Oct. 12, 2010 Notice of Allowance dated Dec. 22, 2011.
JP 2007-519438 filed Jun. 29, 2005 Office Action dated Nov. 30, 2010.
Michaud, Laurent et al, Longevity of Balloon-Stabilized Skin-Level Gastrostomy Device, Journal of Pediatric Gastroenterology and Nutrition, 38: 426-429; Apr. 2004.
PCT/US2005/023297 filed Jun. 29, 2005 International Preliminary Report on Patentability dated Jan. 9, 2007.
PCT/US2005/023297 filed Jun. 29, 2005 Search Report dated May 26, 2006.
PCT/US2005/023297 filed Jun. 29, 2005 Written Opinion dated May 26, 2006.
EP 11742731.0 filed Sep. 4, 2012 extended European Search Report dated Aug. 6, 2013.
U.S. Appl. No. 11/738,979, filed Apr. 23, 2007 Notice of Allowance dated Jun. 17, 2013.
U.S. Appl. No. 12/265,102, filed Nov. 5, 2008 Final Office Action dated Jun. 26, 2013.
U.S. Appl. No. 12/831,644, filed Jul. 7, 2010 Final Office Action dated Nov. 7, 2012.
U.S. Appl. No. 12/831,644, filed Jul. 7, 2010 Non-Final Office Action dated Aug. 1, 2013.
U.S. Appl. No. 12/831,644, filed Jul. 7, 2010 Notice of Allowance dated Dec. 26, 2013.
U.S. Appl. No. 13/024,046, filed Feb. 9, 2011 Non-Final Office Action dated Nov. 29, 2013.
U.S. Appl. No. 13/419,185, filed Mar. 13, 2012 Final Office Action dated Feb. 13, 2014.
U.S. Appl. No. 13/419,185, filed Mar. 13, 2012 Final Office Action dated May 5, 2014.
U.S. Appl. No. 13/419,185, filed Mar. 13, 2012 Non-Final Office Action dated Sep. 3, 2013.

* cited by examiner

METHODS AND SYSTEMS FOR PROVIDING FLUID COMMUNICATION WITH A GASTROSTOMY TUBE

CROSS-REFERENCE TO RELATED APPLICATION

This application claims the benefit of International Application No. PCT/US05/023297, filed 29 Jun. 2005, which claims the benefit of U.S. Provisional Patent Application No. 60/583,703, filed Jun. 29, 2004, the disclosures of each of which are incorporated, in its their entirety, by this reference.

BACKGROUND

Gastrostomy is the creation of a temporary or permanent opening between the stomach and the outer skin in the upper abdominal wall. Gastrostomy tubes are indicated for use when a patient cannot be fed by conventional means and long-term gastric access is needed. Nutrition is either fed, through such a gastrostomy tube, to the patient in a single dose (bolus feeding) or over time using a pump (continuous feeding). Also, the patient may require medication that can be administered directly into the patient's stomach using the gastrostomy tube. This is particularly advantageous in patients, especially children, who often dislike the taste of certain medications.

BRIEF SUMMARY

One aspect of the instant disclosure relates to a system for providing fluid communication with a gastrostomy tube. Particularly, a connector is disclosed that may include a stem upon which an end region of a gastrostomy tube is positionable. As may be appreciated, the stem may define a bore for communicating with a lumen defined by the gastrostomy tube. Further, a locking region extending from the connector and proximate to at least a portion of the stem may be configured to be radially inwardly biased to compress at least a portion of the end region of the gastrostomy tube positionable upon the stem.

In a further aspect of the instant disclosure, another embodiment of a system for providing fluid communication with a gastrostomy tube is disclosed. More specifically, such a system may include a stem upon which an end region of a gastrostomy tube is positionable. Also, the system may include a compression structure comprising a plurality of tines adjacent to at least a portion of the stem may be configured to be radially inwardly biased to compress at least a portion of the end region of the gastrostomy tube positionable upon the stem.

In a further embodiment encompassed by the instant disclosure, a system for providing fluid communication with a gastrostomy tube may include a connector comprising a body including a stem upon which an end region of a gastrostomy tube is positionable, wherein the body further includes at least one recess configured to allow access to at least a portion of the stem. In addition, at least one clip may be configured to be positioned within the recess, the at least one clip comprising at least two movable legs, the at least two movable legs configured to compress at least a portion of the end region of the gastrostomy tube positionable upon the stem.

In another aspect of the instant disclosure, a system for providing fluid communication with a gastrostomy tube including a stem upon which an end region of a gastrostomy tube is positionable is disclosed. In addition, the system may include a plurality of physically separate components configured, when assembled to one another, to compress at least a portion of the end region of the gastrostomy tube positionable upon the stem.

Another aspect of the instant disclosure relates to a gastrostomy tube and feeding tube assembly. Particularly, a feeding tube assembly may be capable of selective coupling to an adaptor in fluid communication with an gastrostomy tube and may be rotatable, when coupled to the adaptor, about a longitudinal axis of the adaptor.

The instant disclosure also relates to a method of coupling a stem to a gastrostomy tube. Specifically, a stem may be positioned within an end region of a gastrostomy tube. Also, a plurality of separate components may be positioned proximate to the end region of the gastrostomy tube and assembled to cause radial inward compression of at least a portion of the end region of the gastrostomy tube.

A further method of coupling a stem to a gastrostomy tube relates to positioning a stem within an end region of a gastrostomy tube, positioning a plurality of tines generally about the circumference of the end region of the gastrostomy tube, and radially inwardly biasing the plurality of tines.

Features from any of the above mentioned embodiments may be used in combination with one another, without limitation. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

Further features of the subject matter of the instant disclosure, its nature, and various advantages will be more apparent from the following detailed description and the accompanying drawings, which illustrate various exemplary embodiments, are representations, and are not necessarily drawn to scale, wherein.

DETAILED DESCRIPTION

Figure 1:
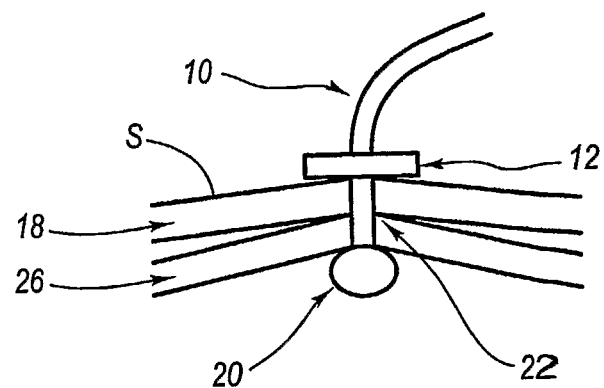
FIG. 1 shows a schematic view of an implanted gastrostomy tube.

Systems, apparatuses, and methods for operably coupling to an implanted gastrostomy tube are disclosed. More particularly, an apparatus or system that may be coupled to an implanted gastrostomy tube to provide fluid communication with such gastrostomy tube is encompassed by the instant disclosure. For example, in one embodiment, FIG. 1 shows a gastrostomy tube 10 that has been implanted within a patient and has a length of between approximately eight to approximately twelve inches of tubing extending from the surface of the patient's abdomen. A gastrostomy tube having such a length may be helpful in clinical environments where a nurse may need to frequently access the device without disturbing the patient. As shown in FIG. 1, the gastrostomy tube 10 may be initially coupled to a patient by an internal bolster 20 and an external bolster 12, which may facilitate creation of and maintain a stoma tract 22 formed between the abdominal wall 18 and the stomach wall 26. As mentioned above, a gastrostomy tube 10 having a relatively long length (e.g., in excess of about six inches extending from the patient) may cause difficulties. For instance, a gastrostomy tube 10 exhibiting a relatively long length may invite removal of the gastrostomy tube 10, particularly if the patient is prone to disturb or dislodge the gastrostomy tube 10 from the stoma, or if the gastrostomy tube 10 becomes caught on something and is inadvertently removed. Therefore, especially if the patient is ambulatory, a shorter gastrostomy tube 10 may be more comfortable and less troublesome. Thus, the instant disclosure contemplates that the gastrostomy tube 10, as shown in FIG. 1, may be shortened and operably coupled to an apparatus or system encompassed by the instant disclosure. Optionally, such coupling may occur after an adhesion or stoma tract 22 forms between an abdominal wall 18 and a stomach wall 26 of a patient.

Figure 2:
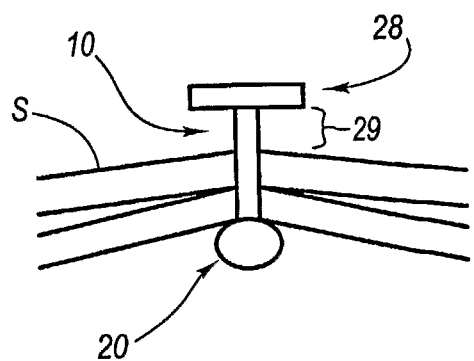
FIG. 2 shows a schematic view of a shortened gastrostomy tube including an adaptor coupled thereto.
Figure 3:
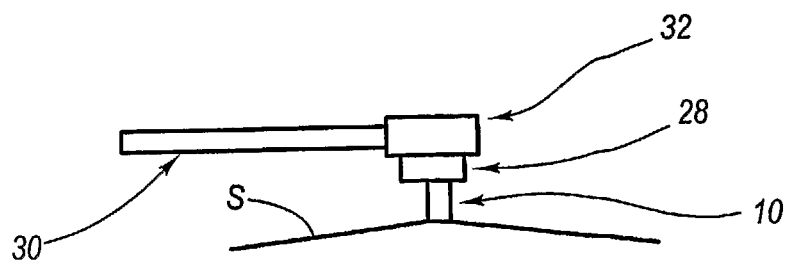
FIG. 3 shows a schematic view of the shortened gastrostomy tube including an adaptor shown in FIG. 2, further including a feeding tube assembly.

Explaining further, conceptually, gastrostomy tube 10 may be shortened (e.g., after a stoma tract forms between an abdominal wall and a stomach of a patient) and an apparatus may be coupled to the shortened gastrostomy tube 10 to provide for fluid communication with the shortened gastrostomy tube. FIG. 2 shows a schematic representation of a shortened gastrostomy tube 10 including an adaptor 28 coupled thereto. A selected, shortened length of the gastrostomy tube 10, as shown in FIG. 2, may provide a gap 29 between the skin surface "S" of the patient and the exposed length of the gastrostomy tube 10. In addition, FIG. 3 shows a schematic representation of the shortened gastrostomy tube 10 including a feeding tube assembly 32 and feeding tube 30 operably coupled to the adaptor 28. Such a method and adaptor 28 may allow for fluid communication between the feeding tube 30 and the gastrostomy tube 10 and may also provide a relatively "low-profile" feeding tube system for long term use, without removing the initially implanted gastrostomy tube 10.

Figure 4:
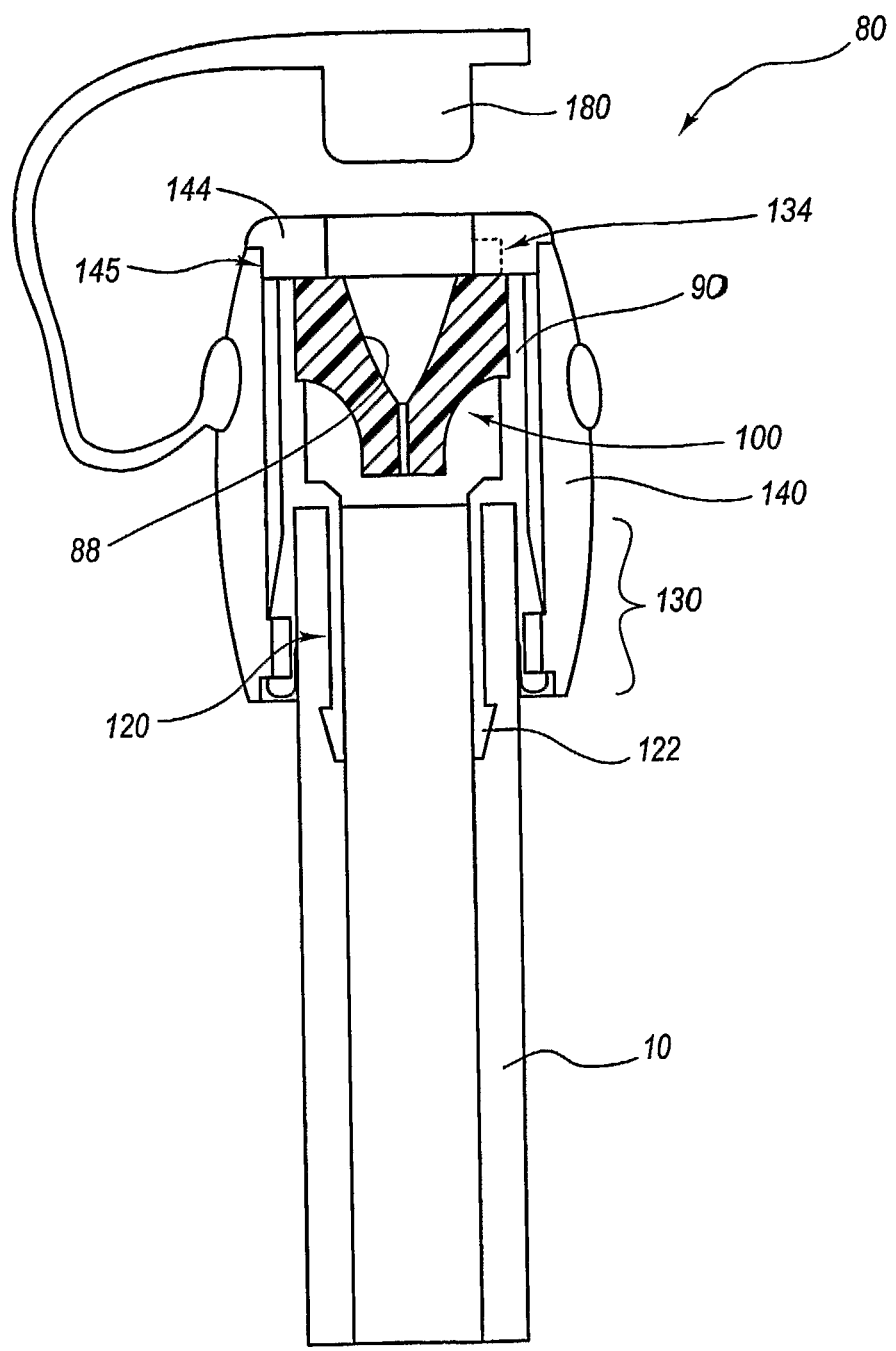
FIG. 4 shows a cross-sectional view of a gastrostomy tube adaptor.

Generally, a system or apparatus for use with a gastrostomy tube may include a stem that is inserted within a lumen of the gastrostomy tube. For example, in one embodiment, FIG. 4 shows a cross-sectional view of an adaptor 80 comprising a connector 90 including a stem 120, which may, optionally, include at least one barb feature 122, inserted within a lumen of a gastrostomy tube 10. In addition, adaptor 80 includes a one-way valve 100 positioned within a bore of the connector 90 and a compression sleeve 140 positioned about the connector 90. One-way valve 100 is shown embodying a so-called "duckbill" or Heimlich valve; however, other types of one-way valves (flapper-type, ball-type, etc.), as known in the art, may be employed for controlling fluid communication with gastrostomy tube 10. Such a one-way valve may be configured to prevent reflux (e.g., gastric liquid or gas) from exiting the gastrostomy tube 10 from a stomach. The connector 90, as shown in FIG. 4, also includes locking region 130, which is configured to be radially displaced or biased toward the gastrostomy tube 10 to compress the gastrostomy tube 10 between a portion of the stem 120 and the locking region 130. In one embodiment, locking region 130 may comprise a plurality of circumferentially-spaced (about the stem 120) tines or prongs (e.g., a collet or similar structure) or, in another embodiment, locking region 130 may comprise a substantially tubular shape. Explaining further, the compression sleeve 140 may be positioned about the locking region 130 of the connector 90 and may be configured to generate a radially inward force upon the locking region 130. Such a radially inward force may, in turn, bias at least a portion of the locking region 130 toward the gastrostomy tube 10 to effectively couple the gastrostomy tube 10 to the stem 120. Optionally, as shown in FIG. 4, stem 120 may include at least one barb 122. Further, a connector cap 144 may be affixed to compression sleeve 90 by way of a connection structure 145 (e.g., a so-called luer connection or any other connection structure as known in the art) or, such a feature may be incorporated into the connector 90. In another embodiment, compression sleeve 140 and connector cap 144 may be combined into a single piece. Further, an engagement structure 134 (shown in FIG. 4 as a recessed region) may comprise a so-called snap-lock, threaded connection, or any other connection structure as known in the art. Engagement structure 134 may be formed in connector cap 144, connector 90, or compression sleeve 140 and may be configured to operably couple a feeding tube to the adaptor 80. During use, a feeding tube extension or assembly may be coupled to the adaptor 80 by contact with tapered surface 88 of one-way valve 100. Optionally, a sealing element (e.g., an O-ring) may be positioned between tapered surface 88 and a surface of a feeding tube assembly to provide a fluid-tight (i.e., hydraulic, pneumatic, or both hydraulic and pneumatic) seal between the surfaces. Such contact may also cause the one-way valve 100 to at least partially open; thus, fluid communication through the one-way valve may be facilitated. A closure element 180 may be employed to close the interior bore of the adaptor 80 while not in use.

Figure 5:
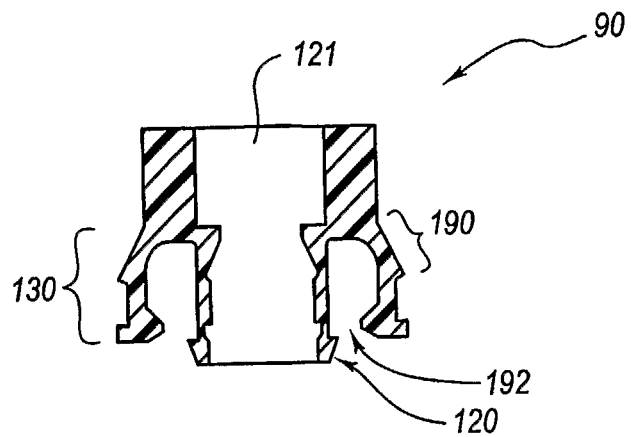
FIG. 5 shows a partial, schematic, side cross-sectional view of one embodiment of a gastrostomy tube connector.

FIG. 5 shows a partial, schematic, side cross-sectional view of another embodiment of connector 90, particularly, stem 120 and locking region 130. The locking region 130, as shown in FIG. 5, has at least one tapered feature 190 configured to interfere with an interior surface of compression sleeve 140 (FIG. 4) when the compression sleeve 140 (FIG. 4) is assembled to the connector 90. Accordingly, such interference may cause the locking region 130 to be deformed or displaced radially inwardly, as discussed above. In addition, at least one protrusion 192 may be formed upon locking region 130. Protrusion 192 may extend generally radially inwardly and may be generally pointed, as shown in FIG. 5. Such a configuration may facilitate locking of a gastrostomy tube 10 (FIG. 4) upon the stem 120. The instant disclosure further contemplates that a plurality of barbs may be formed, at selected positions and having selected configurations, respectively, on the stem 120 and may allow for formation of a robust mechanical and fluid-tight coupling between a gastrostomy tube 10 (FIG. 4) and a bore 121 defined by the stem 120.

Figure 6:
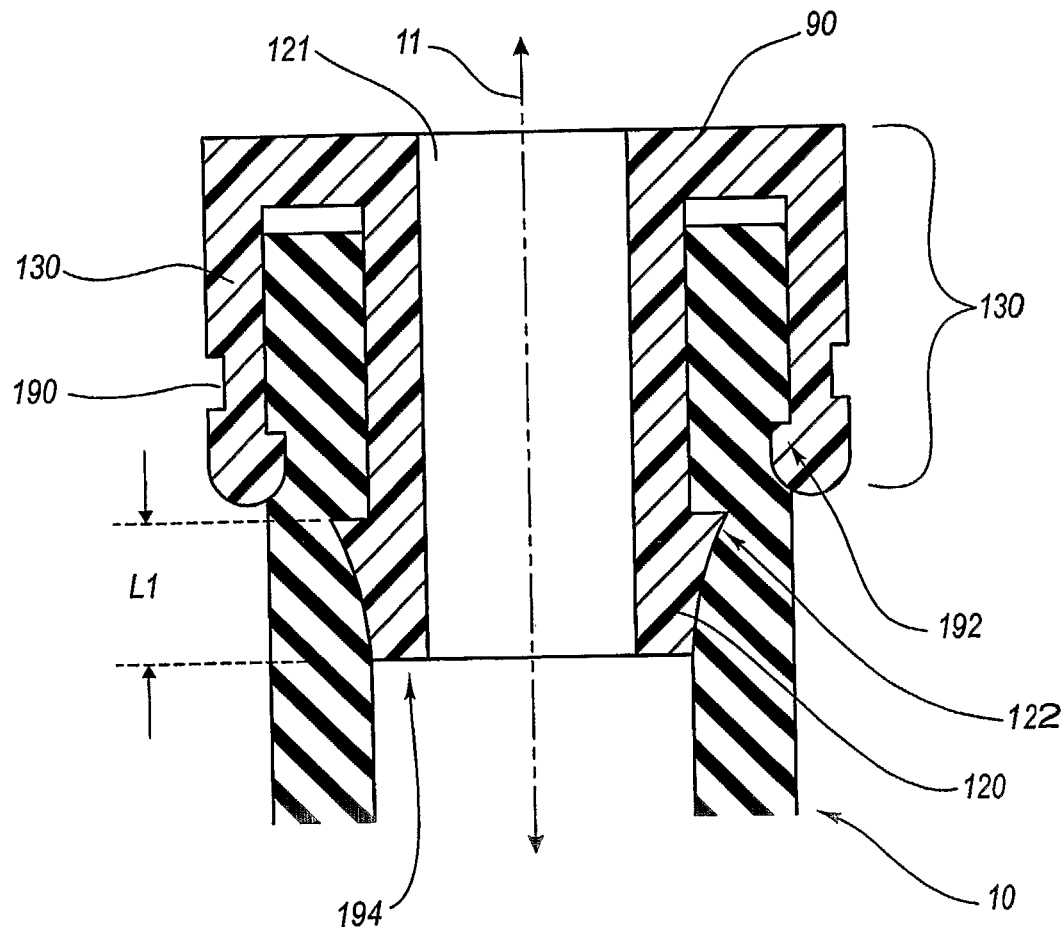
FIG. 6 shows a partial, schematic, side cross-sectional view of another embodiment of a gastrostomy tube connector.

In a further aspect of the instant disclosure, at least one protrusion formed upon a locking region of a connector may be positioned proximate to a maximum radial extent of a barb formed on a stem of a connector. For example, in one embodiment, FIG. 6 shows a partial, schematic, side cross-sectional view of a stem 120 that has a barb 122 that includes a maximum radial extent located at a longitudinal position "L1" (with respect to a longitudinal axis 11 of stem 120) from a distal surface 194 of the connector 90. Further, protrusion 192 may be located proximate to the maximum radial extent of barb 122. Also, as shown in FIG. 6, protrusion 192 may be located at a longitudinal distance from distal surface 194 of connector 90 that exceeds the longitudinal distance between the maximum radial extent of barb 122 and distal surface 194 of connector 90. Such a configuration may provide a relatively robust coupling and fluid-tight connection between the bore 121 defined by stem 120 and the gastrostomy tube 10. As illustrated in FIGS. 4-6 the locking region 130 extends from and is integral with the connector 90.

Figure 7:
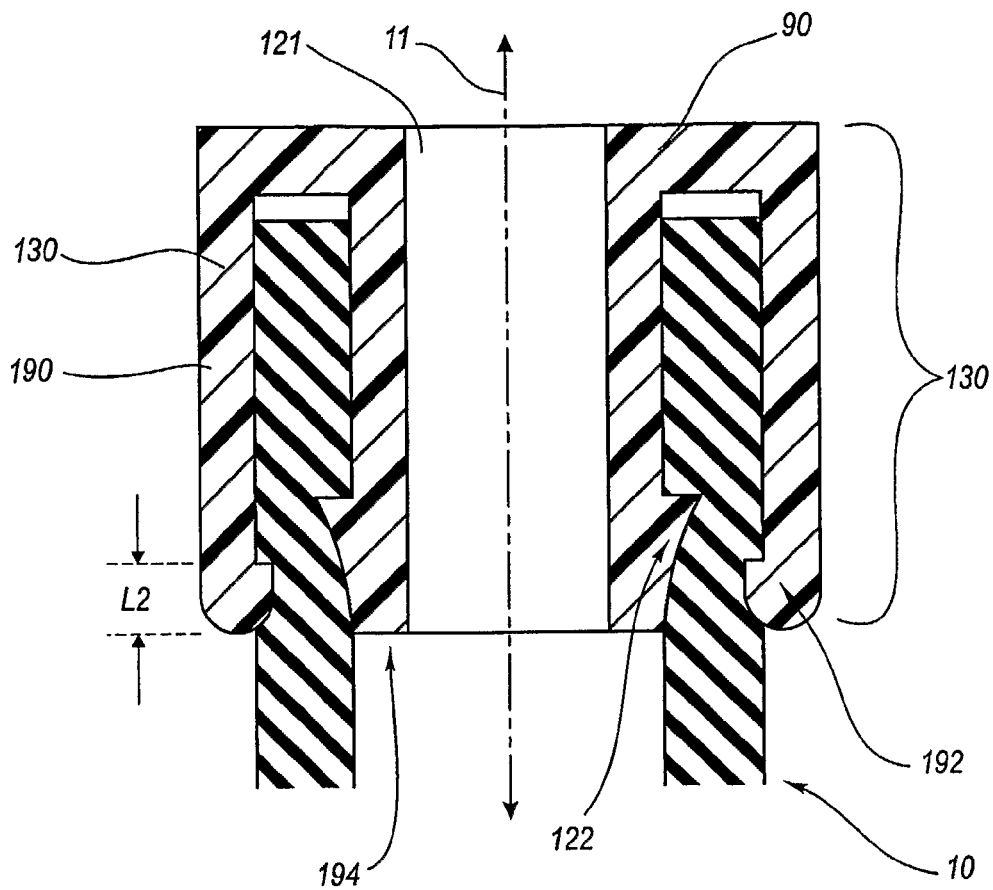
FIG. 7 shows a partial, schematic, side cross-sectional view of a further embodiment of a gastrostomy tube connector.

In another embodiment, at least one protrusion formed upon a locking region of a connector may be positioned proximate to a distal surface of the connector. For example, in one embodiment, FIG. 7 shows a partial, schematic, side cross-sectional view of a locking region 130 that has a barb 122. Further, protrusion 192 may be located proximate to the distal surface 194 of the connector 90. Also, as shown in FIG. 7, protrusion 192 may be located at a longitudinal distance "L2" from distal surface 194 of connector 90 that is less than the longitudinal distance between the maximum radial extent of barb 122 and distal surface 194 of connector 90. Such a configuration may provide a relatively robust coupling and fluid-tight connection between the bore 121 defined by stem 120 and the gastrostomy tube 10.

Figure 8:
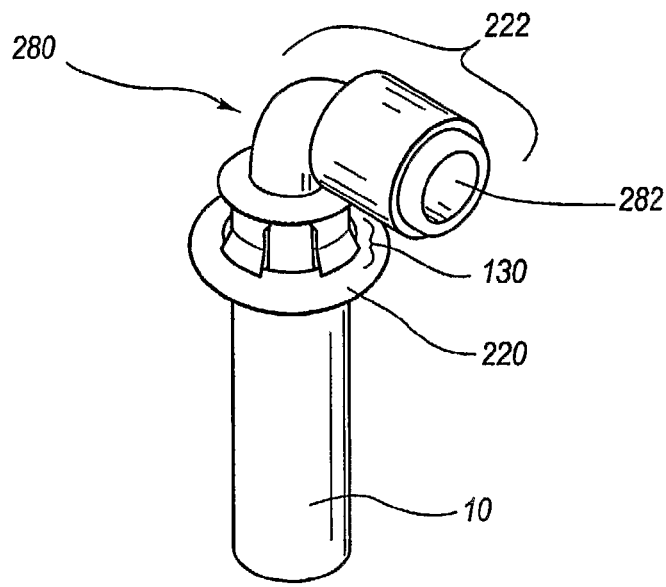
FIG. 8 shows a perspective view of an embodiment of a gastrostomy tube adaptor.
Figure 9:
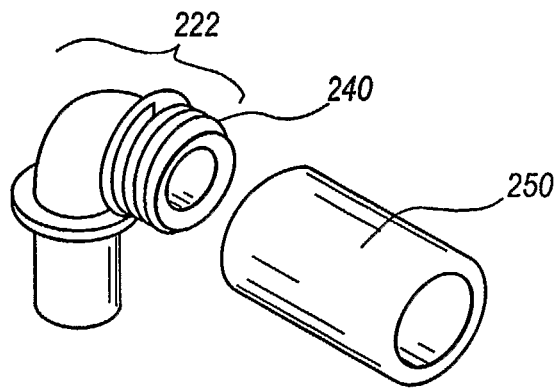
FIG. 9 shows a perspective view of another embodiment of a gastrostomy tube adaptor.

FIG. 8 shows a perspective view of an embodiment of an adaptor 280. More specifically, adaptor 280 may be configured generally as described above in relation to adaptor 80, but may also include an angled portion 222 (e.g., forming a right angle with respect to a longitudinal axis of the gastrostomy tube 10). As described above, locking region 130 may be compressed toward the gastrostomy tube 10 by a compression sleeve 220. Since compression sleeve 220 may be difficult to position over angled portion 222 of adaptor 280, compression sleeve 220 may be embody a clam-shell design or may be separate pieces that lock or interconnect to one another around gastrostomy tube 10, subsequent to positioning of a stem of adaptor 280 within gastrostomy tube 10, as discussed below. Of course, adaptor 280 may also include a one-way valve, as discussed above, and may include features that to allow attachment of a straight feeding tube to port opening 282 to achieve a low-profile design. FIG. 9 shows a perspective view of another embodiment of an angled portion 222 of an adaptor including a threaded port 240 and a threaded housing 250 for attachment to the threaded port 240. Further, threaded housing 250 may include a one-way valve. Such a configuration may be desirable so that the one-way valve may be removed and replaced if needed.

Figure 10:
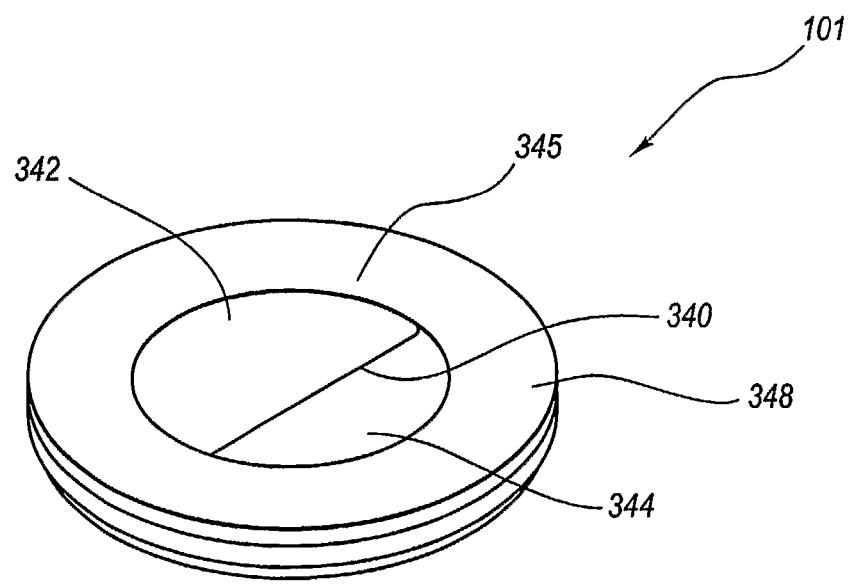
FIG. 10 shows a perspective view of a one-way valve.
Figure 11:
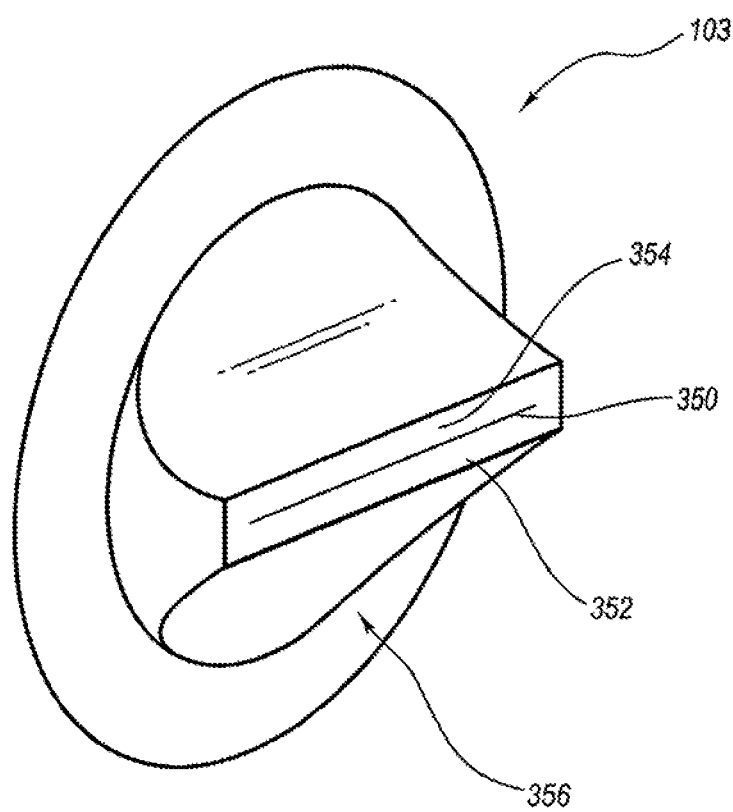
FIG. 11 shows a perspective view of another embodiment of a one-way valve.
Figure 12:
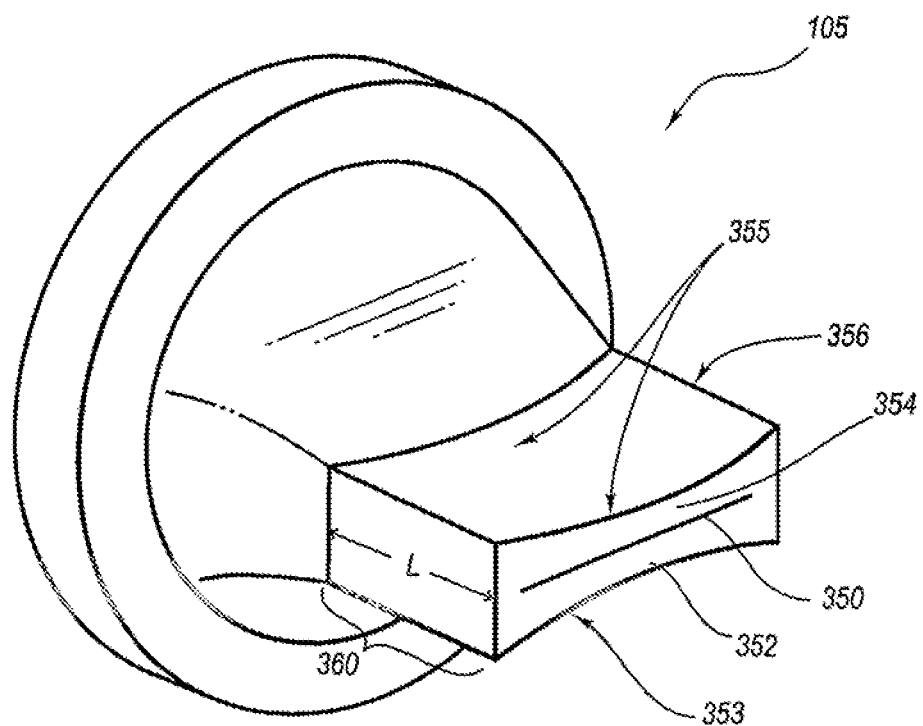
FIG. 12 shows a perspective view of yet a further embodiment of a one-way valve.

In further detail, FIG. 10 shows a one-way valve 101 in a perspective view that comprises a frame element 348 (e.g., a substantially cylindrical frame) defining an opening 345 and including a first flap 342 extending over about half of the cross-sectional area of the opening 345 and a second flap 344 extending over the remaining cross-sectional area of the opening 345. Further, first flap 342 and second flap 344 may contact one another along mating line 340 (i.e., a slit) and may be configured to generally resist the flow of fluid between first flap 342 and second flap 344. However, one-way valve 101 may be configured so that fluid flow is allowed between first flap 342 and second flap 344 (through slit or mating line 340) when a syringe or other suitably shaped device applies a force to flaps 342 and 344. Thus, a syringe may engage flaps 342 and 344 so that the edges (forming mating line 340), respectively, separate from one another to allow fluid flow between flaps 342 and 344. FIG. 11 shows a perspective view of another embodiment of a one-way valve 103, configured as a duckbill valve, including protruding feature 356, which is separated, at its distal end, along mating line 350 into a first half 352 and a second half 354. Similar to one-way valve 101, first half 352 and second half 354 are configured to prevent fluid flow therebetween (i.e., along mating line 350), unless a syringe or other suitably shaped device contacts the first half 352 and second half 354. In yet a further embodiment of a one-way valve, FIG. 12 shows a perspective view of another one-way valve 105 (configured as a duckbill valve) including a land area 360 of protruding feature 356 having a length "L" and concave side surfaces 355 and 353. Repeated use and stresses in the material forming one-way valve 105 may cause the mating line 350 to remain at least partially open due to the material "creep" or permanent deformation, as known in the art. Configuring the side surfaces 353 and 355 to exhibit a concave shape may resist such material creep and may also facilitate or bias the one-way valve 105 to close.

Figure 13:
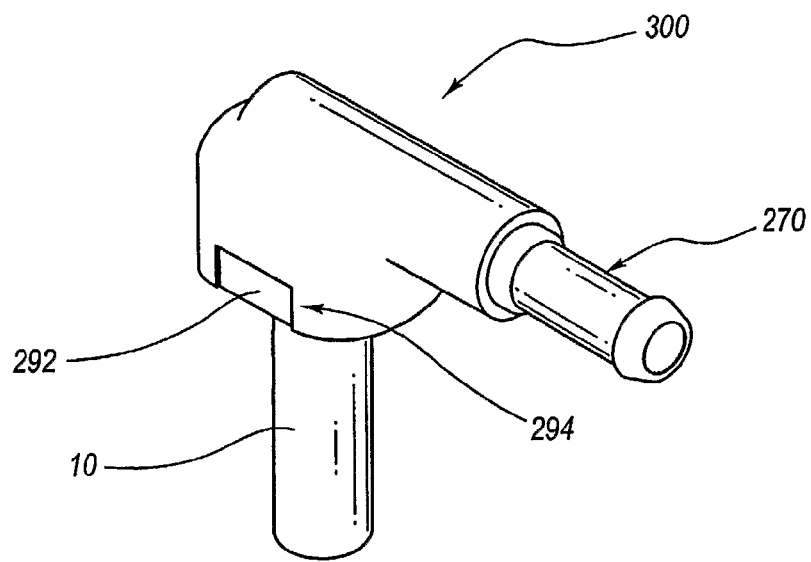
FIG. 13 shows a perspective view of a gastrostomy tube adaptor including compression clips.
Figure 14:
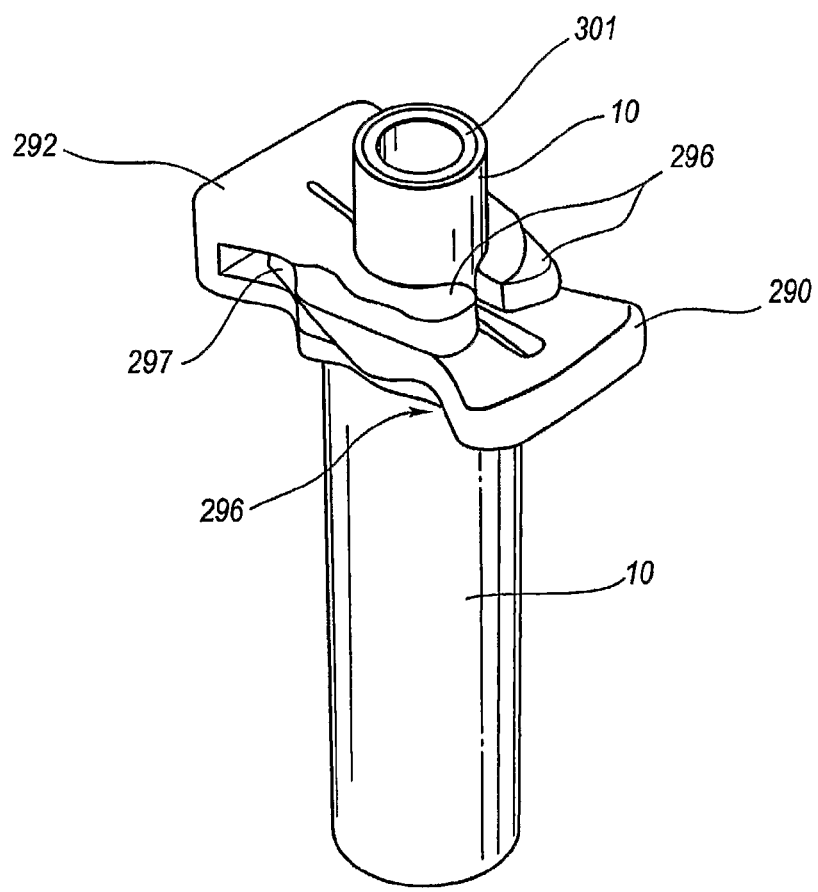
FIG. 14 shows a perspective view of compression clips positioned about a gastrostomy tube.
Figure 15:
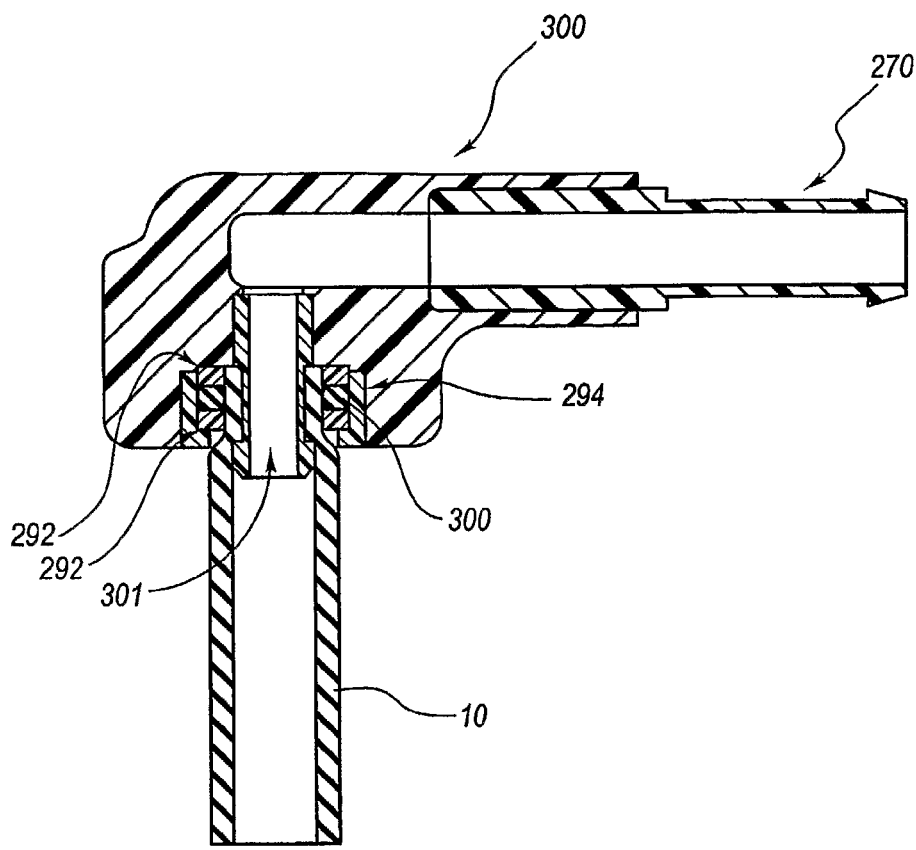
FIG. 15 shows a schematic, side cross-sectional view of the adaptor shown in FIG. 13.

FIG. 13 shows a perspective view of a further embodiment of an adaptor 300 including an outlet port 270 that forms an angle (i.e., is not generally aligned with) with respect to a gastrostomy tube 10 to which it is coupled. In addition, recess 294 may be formed laterally (i.e., substantially perpendicular to a longitudinal axis of gastrostomy tube 10) through the body of adaptor 300 to allow access to the end region of gastrostomy tube 10 positioned upon a stem (discussed below) of the adaptor 300. As shown in FIG. 13, compression clip 292 (and compression clip 290 shown in FIGS. 14 and 15, discussed below) may be positioned within recess 294 and may radially inwardly compress and mechanically couple gastrostomy tube 10 to the adaptor 300. In further detail, FIG. 14 shows a perspective view of compression clips 290 and 292 positioned about gastrostomy tube 10 and stem 301 of adaptor 300. As shown in FIG. 14, compression clip 292 may include a pair of upper movable arms 296 and a pair of lower movable arms 296, wherein each set of movable arms has an arcuate surface for contacting at least a portion of the gastrostomy tube 10 to compress the portion of the gastrostomy tube 10 radially inwardly against stem 301. Also as shown in FIG. 14, compression clip 290 may include a pair of movable arms 297 and may be positioned longitudinally between the upper and lower pair of movable arms 296 of compression clip 292. FIG. 15 shows a schematic side cross-sectional view of adaptor 300 illustrating the location of compression clips 290 and 292 positioned within recess 294 and about gastrostomy tube 10 and stem 301.

Figure 16:
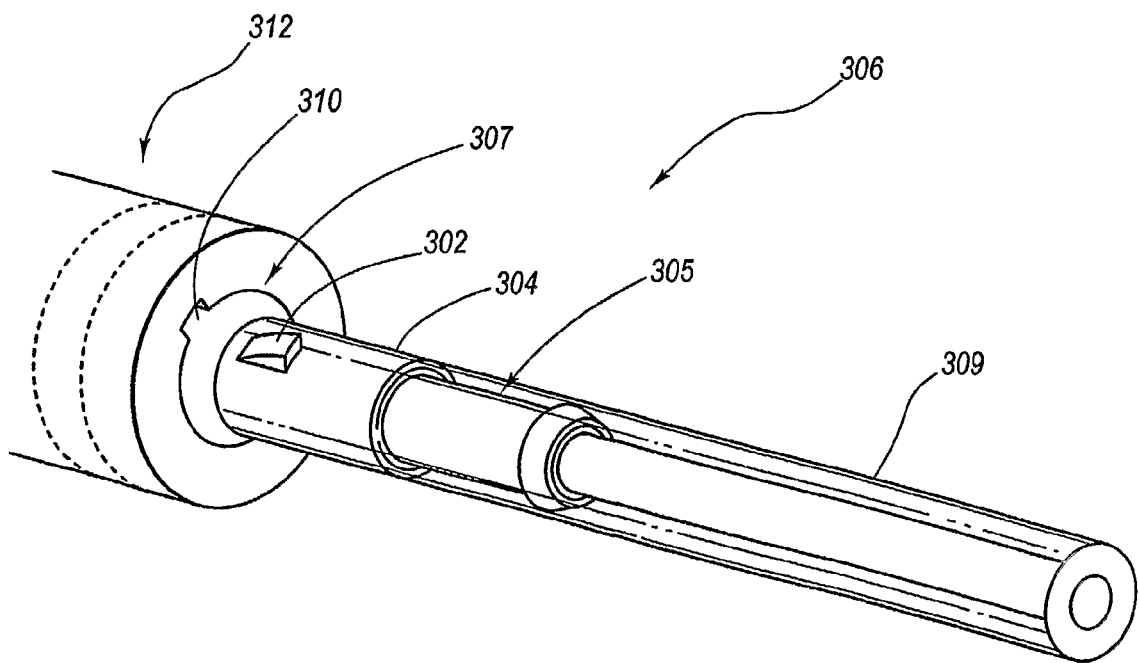
FIG. 16 shows a perspective view of a feeding tube assembly configured to mechanically couple to a gastrostomy tube apparatus.

FIG. 16 shows a perspective view of a feeding tube assembly 306 including a coupler 304 with a radially protruding feature 302 and a stem portion 305 and feeding tube 309 extending from the stem portion 305. Coupler 304 may be configured for mechanically coupling to a connector 312 (e.g., connector 90 as discussed above or a base element as discussed below). More particularly, protruding feature 302 may align with groove 310 formed in recess 307 of the connector 312. Further, protruding feature 302 may fit into or otherwise engage a lip or other feature (e.g., another recess such as recess 134 as shown in FIG. 4) formed into the surface of recess 307.

Figure 17:
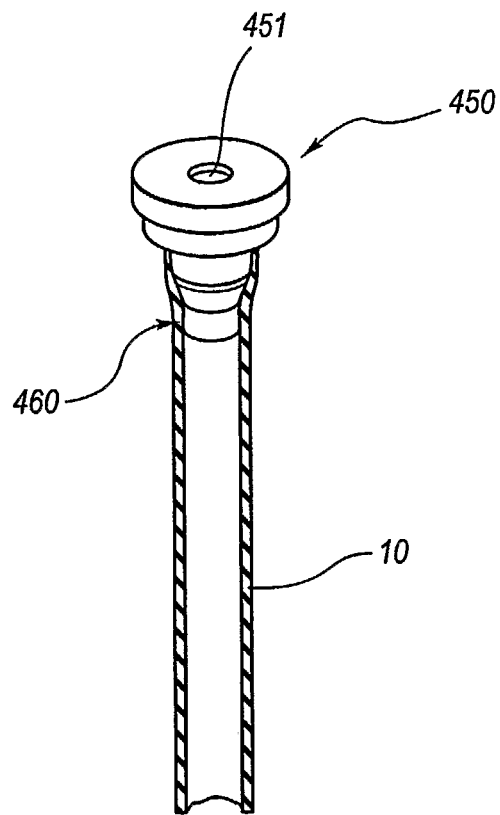
FIG. 17 shows a perspective view of a base element including a stem and a gastrostomy tube positioned upon the stem.

Another aspect of the instant disclosure relates to a gastrostomy tube adaptor that has a clamping mechanism that may be installed upon a base element including a stem. More particularly, a clamping mechanism may be configured to at least partially circumferentially contact and correspondingly radially compress a gastrostomy tube onto a stem of the base element. For example, a clamping mechanism may include two separate pieces that couple to one another to compress a gastrostomy tube onto a stem of the base element. More generally, a system for providing fluid communication with a gastrostomy tube may include a plurality of separate pieces, which, when assembled, are configured to compress at least a portion of an end region of a gastrostomy tube positionable upon a stem. Such a configuration may simplify the design of an adaptor for converting a gastrostomy tube to a low-profile in comparison to the adaptor described above including a connector with a locking region. Explaining further, a common base element may be used in combination with a selected clamping apparatus to provide flexibility. In one embodiment, FIG. 17 shows a perspective view of base element 450 including a stem 460 positioned within a gastrostomy tube 10. Bore 451 of base element 450 is in fluid communication with the lumen of gastrostomy tube 10. As explained below, a feeding tube may be selectively coupled to base element 450 and may be used to provide nourishment into a stomach of a patient through the gastrostomy tube 10.

Figure 18:
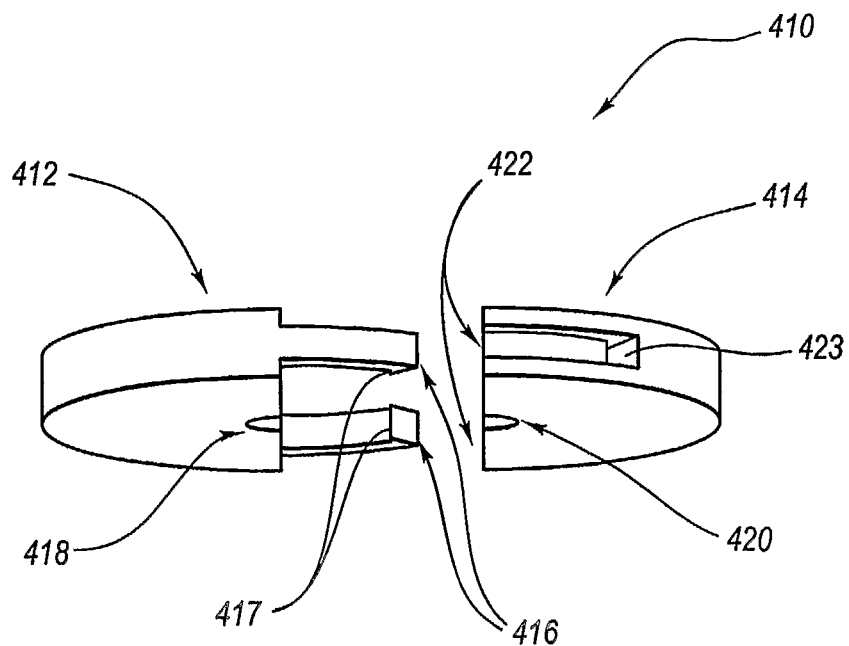
FIG. 18 shows a perspective view of a clamping apparatus.
Figure 19:
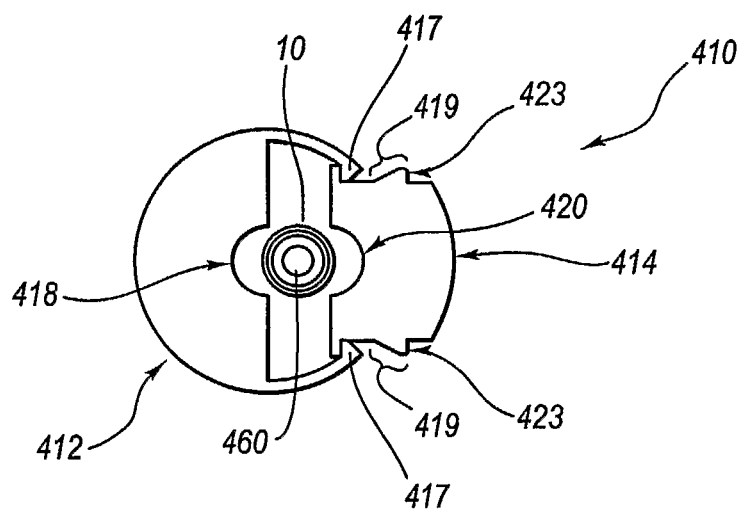
FIG. 19 shows a schematic, top-elevation view of the clamping apparatus shown in FIG. 18.
Figure 20:
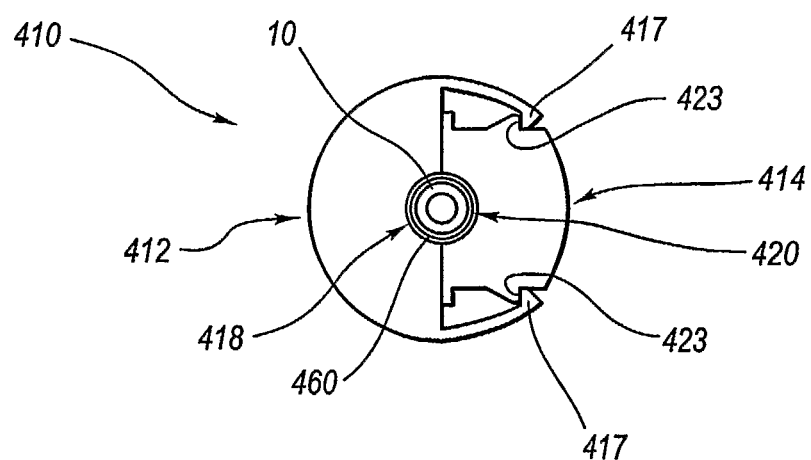
FIG. 20 shows a schematic, top-elevation view of the clamping apparatus shown in FIG. 18, when assembled.
Figure 21:
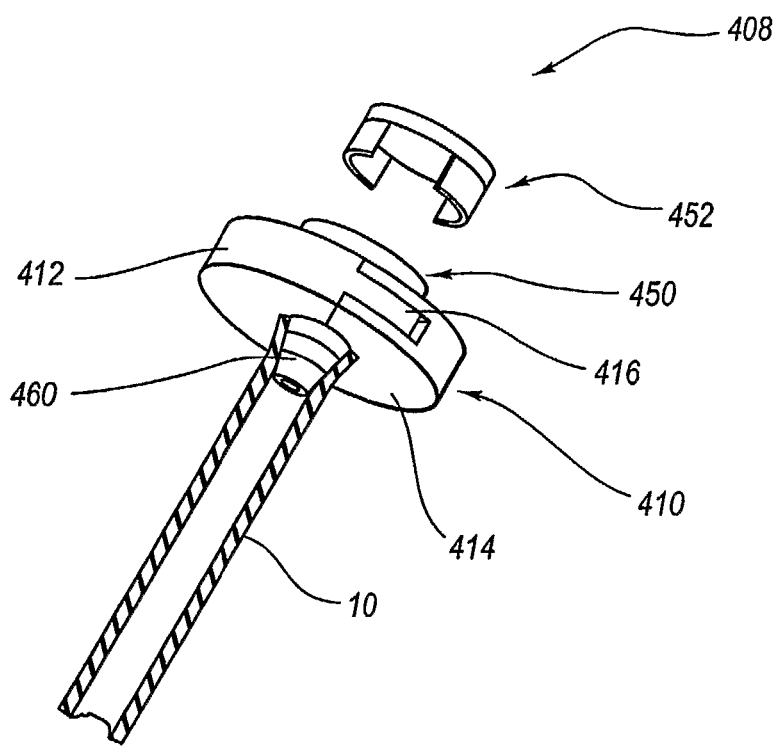
FIG. 21 shows a perspective view of a gastrostomy tube assembly including a clamping apparatus as shown in FIGS. 18 through 20.

FIG. 18 shows a perspective view of a clamping apparatus 410 including a first half 412 and a second half 414. First half 412 includes locking arms 416, each of locking arms 416 including a protruding feature 417 for engaging a suitably shaped engagement surface 423 formed in grooves 422 of second half 414. First half 412 and second half 414 may each include an arcuate surface 418, 420, respectively, configured for compressing a portion of a gastrostomy tube positioned upon a stem about which the clamping apparatus 410 is positioned. In further detail, FIG. 19 shows a schematic, top-elevation view of clamping apparatus 410 positioned about gastrostomy tube 10 and stem 460. As may be appreciated, upon movement of first half 412 and second half 414 toward one another, protruding features 417 may move along tapered regions 419, respectively, and may effectively lockingly engage engagement surfaces 423 of second half 414. FIG. 20 shows a schematic, top-elevation view of first half 412 and second half 414 coupled to one another via protruding features 417 engaging engagement surfaces 423. In addition, it may be appreciated that the gastrostomy tube 10 may be compressed by the arcuate surfaces 418, 420 (shown as substantially semicylindrical in FIGS. 18 and 19) against stem 460. FIG. 21 shows a perspective view of a gastrostomy tube assembly 408 including the clamping apparatus 410 installed upon base element 450 including stem 460 positioned within gastrostomy tube 10. Optionally, a closure element 452 may be coupled to the base element 450 to close the bore extending therethrough. Also, optionally, a one-way valve may be positioned within the base element 450. The first half 412 of the system and the second half 414 of the system may include complementary locking features, e.g., protruding features 417, configured to engage one another to form a circular arcuate surface 418, 420.

Figure 22:
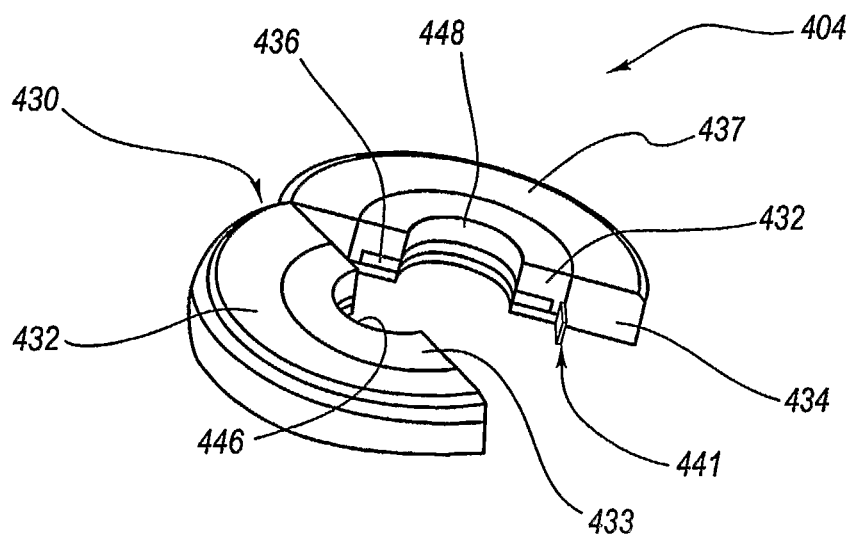
FIG. 22 shows a perspective view of another embodiment of a clamping apparatus.
Figure 23:
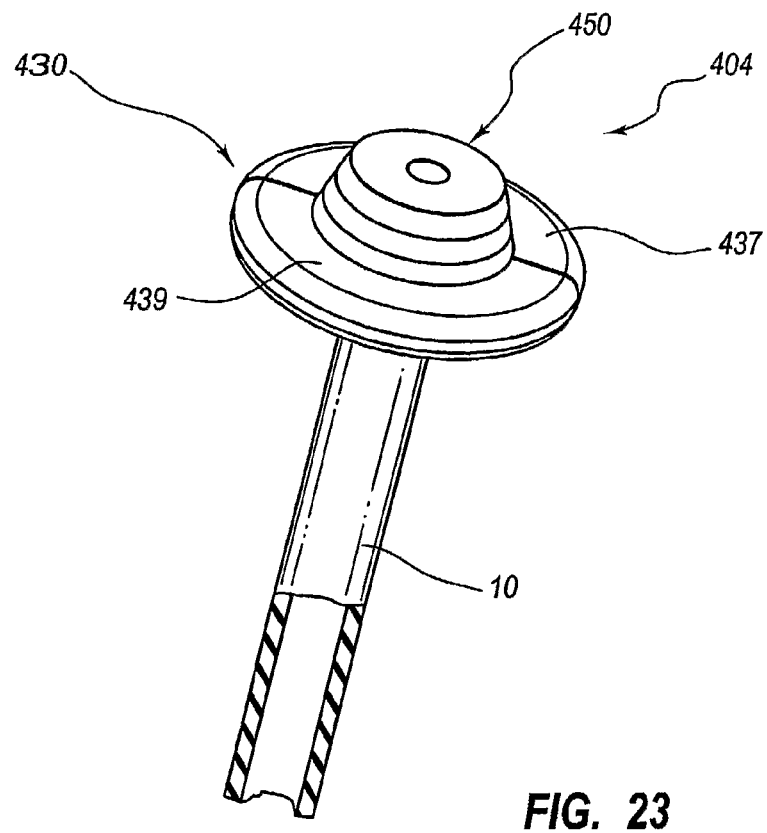
FIG. 23 shows a perspective view of the clamping apparatus shown in FIG. 22 assembled to a base element.
Figure 24:
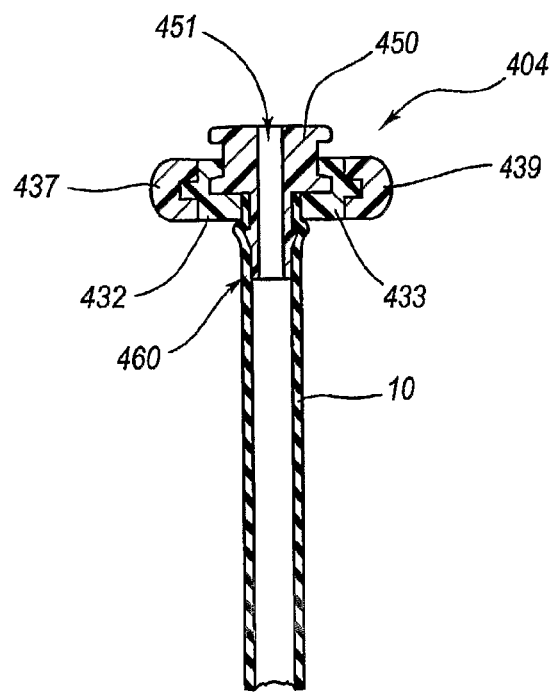
FIG. 24 shows a schematic, side cross-sectional view of the assembly shown in FIG. 23.

FIG. 22 shows a perspective view of another embodiment of a clamping apparatus 404 including a hinge mechanism 430, clamp elements 432, 433, and halves 437, 439. More specifically, halves 437, 439 may comprise a pliant material such as silicone, while clamp elements 432, 433 may comprise a relatively rigid material such as a rigid plastic (e.g., polyethylene, polypropylene, etc.) or a metal. Such a configuration may provide a relatively comfortable gastrostomy tube apparatus for a patient's use. Optionally, halves 437, 439 may substantially surround clamp elements 432, 433. Arcuate surfaces 448, 446 (shown as substantially semicylindrical) of clamp elements 432, 433 may be configured for compressing a gastrostomy tube against a stem about which the clamping apparatus 404 is positioned. Annular recess 436 may be configured for accepting, upon placement of the clamping apparatus about a gastrostomy tube within which a base element is positioned, a corresponding annular flange of a base element. Thus, each of halves 437, 439 may be separated by rotation about hinge mechanism 430 and positioned about a gastrostomy tube. As shown in FIG. 22, clamp element 432 includes a locking feature 441 that extends from clamp element face 434 for securing clamp element 432 to clamp element 433. Accordingly, clamp elements 432, 433 may include complementary locking features (e.g., protruding features, pins, or any other locking features as known in the art) configured to secure clamp elements 432, 433 to one another. FIG. 23 shows a perspective view of clamping apparatus 404 assembled to the base element 450. Further, FIG. 24 shows a schematic side cross-sectional view of clamping apparatus 404 assembled to base element 450. As shown in FIG. 24, clamping elements 432, 433 may be configured to compress gastrostomy tube 10 onto stem 460 of base element 450. Thus, bore 451 of base element 450 may be in fluid communication with a lumen of gastrostomy tube 10. Optionally, base element 450 may be configured to accept a one-way valve configured to allow fluid to flow in a direction toward or into gastrostomy tube 10, but inhibit fluid flow from gastrostomy tube 10 toward base element 450. The first half 437 of the system and the second half 439 of the system may include complementary locking features configured to engage one another to form a circular arcuate surface 446, 448.

Figure 25:
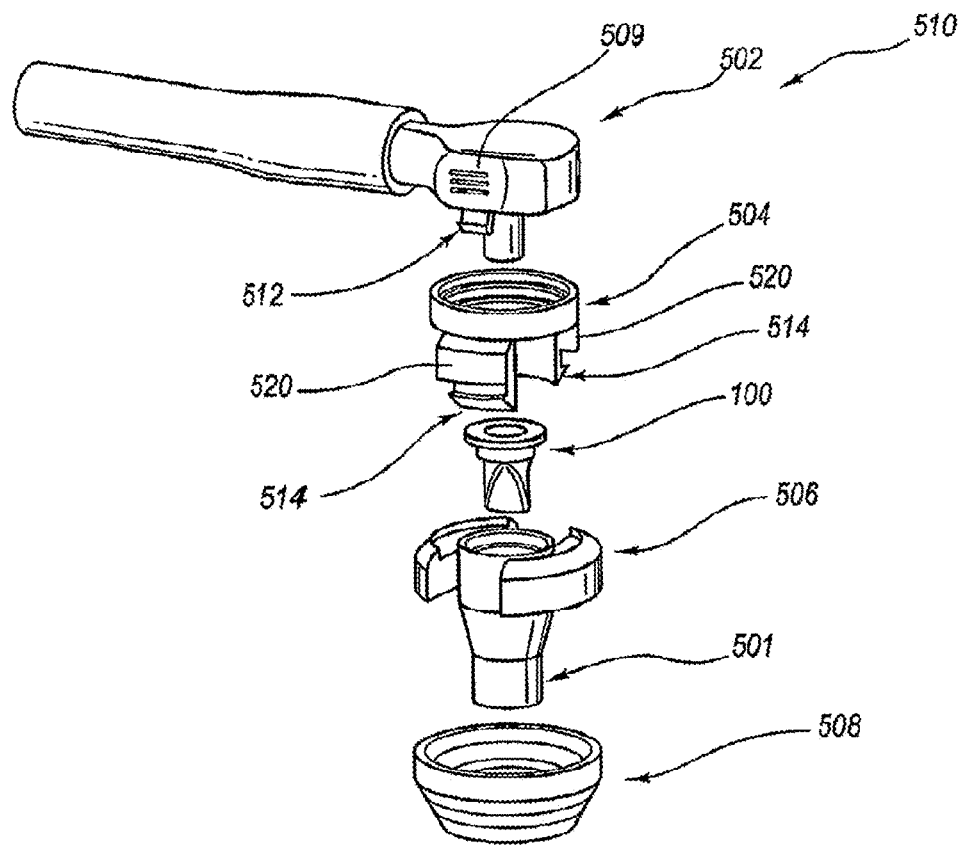
FIG. 25 shows an exploded assembly view of another embodiment of a gastrostomy tube adaptor assembly.
Figure 26:
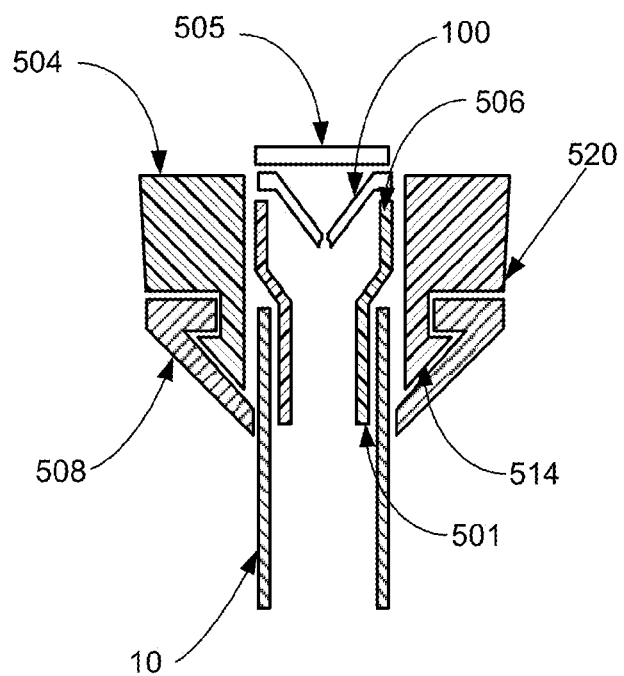
FIG. 26 shows a partial, schematic, side cross-sectional view of the assembly shown in FIG. 25.

FIG. 25 shows an exploded assembly view of another embodiment of a gastrostomy tube adaptor assembly 510 including feeding tube assembly 502, locking hub 504, one-way valve 100, base element 506, and compression ring 508. In further detail, a gastrostomy tube may be positioned about stem 501 of base element 506 and locking elements 514 of locking hub 504 may each engage a complementary engagement feature formed within compression ring 508. More specifically, longitudinal movement between locking hub 504 and compression ring 508 may cause locking elements 514 to engage or otherwise be retained by a complementary engagement feature formed within compression ring 508. Also, regions 520 may be configured to move locking elements 514 inwardly upon application of force thereon (e.g., by squeezing of a hand of a user) to release each of the locking elements 514 from a respective complementary engagement feature formed within compression ring 508. Further, compression ring 508 may be configured to compress (e.g., radially inwardly compress) a gastrostomy tube positioned between the compression ring 508 and the stem 501 of the base element 506. For example, FIG. 26 shows a schematic side cross-sectional view of an assembly of locking hub 504, one-way valve 100, base element 506, and compression ring 508, as shown in FIG. 25. As shown in FIG. 26, locking hub 504 includes an annular recess 505 configured for engaging locking features 512 (FIG. 25) of feeding tube assembly 502 (FIG. 25). Such a configuration, when locking hub 504 and feeding tube assembly 502 (FIG. 25) are coupled to one another, may allow for rotation of feeding tube assembly 502 (FIG. 25) with respect to locking hub 504. Also, pressure applied generally to region 509 (FIG. 25) may cause locking feature 512 to release from annular recess 505. Thus, feeding tube assembly 502 (FIG. 25) may be selectively released from locking hub 504 when desired. Also, as shown in FIG. 26, compression ring 508 may be configured for inwardly radially compressing at least a portion of an end region of gastrostomy tube 10 positioned upon stem 501 of base element 506.

Figure 27:
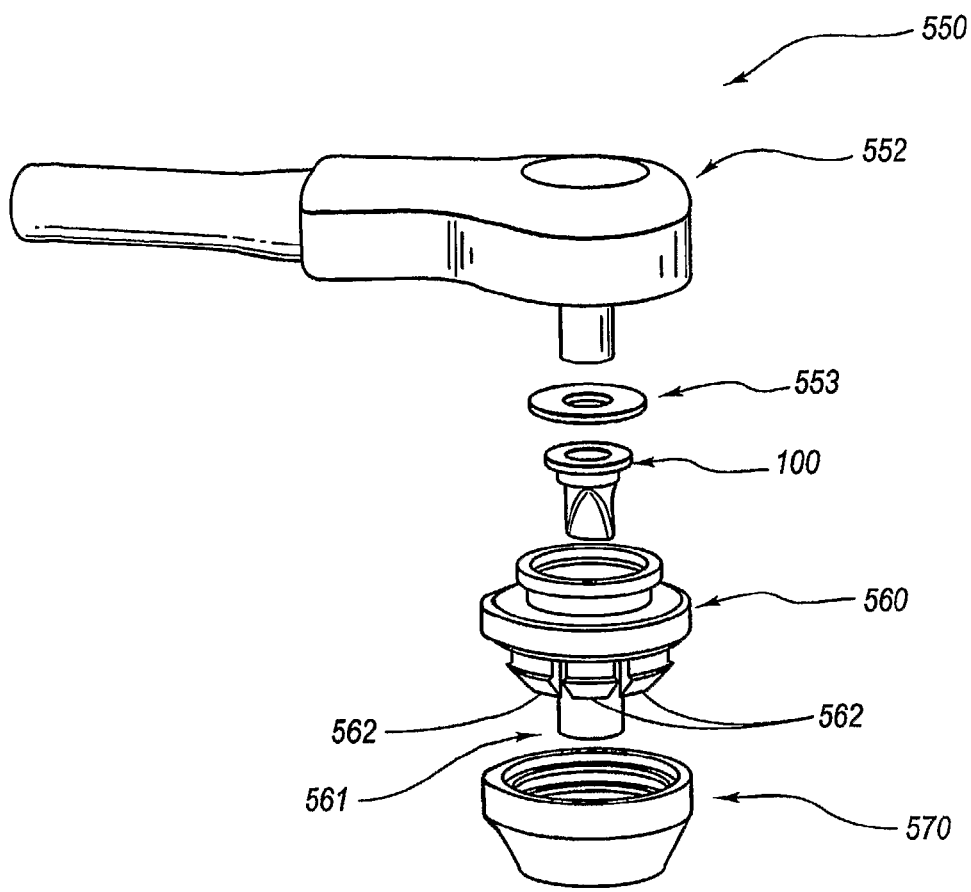
FIG. 27 shows an exploded assembly view of a further embodiment of a gastrostomy tube adaptor assembly.
Figure 28:
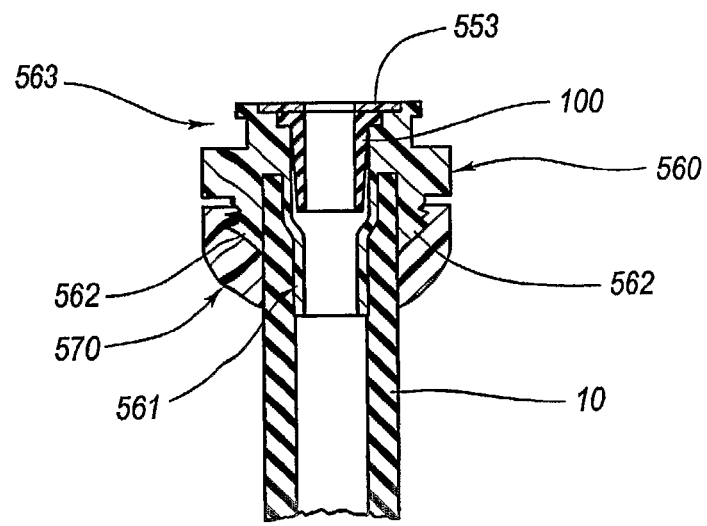
FIG. 28 shows a partial, schematic, side cross-sectional view of the assembly shown in FIG. 27.

FIG. 27 shows an exploded assembly view of a gastrostomy tube adaptor assembly 550 including feeding tube assembly 552, washer element 553, one-way valve 100, base element 560, and compression ring 570. More specifically, as shown in FIG. 27, base element 560 includes tines 562 extending longitudinally from base element 560 that have a threaded exterior surface. Tines 562 extend from base 560 proximate to stem 561 and may be configured to be radially inwardly biased to compress at least a portion of an end region of a gastrostomy tube positioned about stem 561 of base element 560. Thus, compression ring 570 may include a threaded interior surface for threading along the threaded exterior surface of tines 562 so that tines 562 are biased radially inwardly. Thus, FIG. 28 shows a schematic side cross-sectional view of base element 560, washer element 553, one-way valve 100, compression ring 570, and gastrostomy tube 10. As shown in FIG. 28, compression ring 570 may inwardly radially compress tines 562 toward the end region of gastrostomy tube 10 positioned upon stem 561 of base element 560. Such a configuration may provide an effective and fluid-tight coupling between the base element 560 and the gastrostomy tube 10. In addition, feeding tube assembly 552 (FIG. 27) may be configured to couple to base element 560. In one embodiment, feeding tube assembly 552 (FIG. 27) may be configured to couple to an annular recess 563 (FIG. 28) formed in base element 560. In another embodiment, base element 560 can be configured similarly to region 520, illustrated in FIG. 25. In such an embodiment base element 560 can act as a release configured to move the plurality of tines 562 inward upon application of a force to the base element 560. Force on the release (base element 560) can release the compression ring 570, or in another embodiment, a compression sleeve such as compression sleeve 220 illustrated in FIG. 8.

Figure 29:
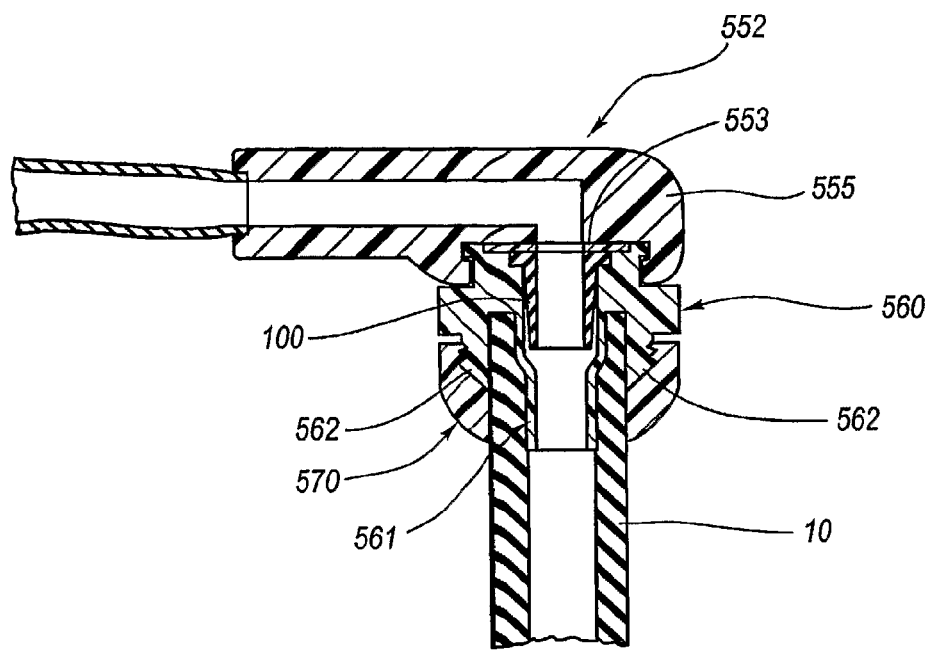
FIG. 29 shows a schematic, side cross-sectional view of one embodiment of a feeding tube assembly.
Figure 30:
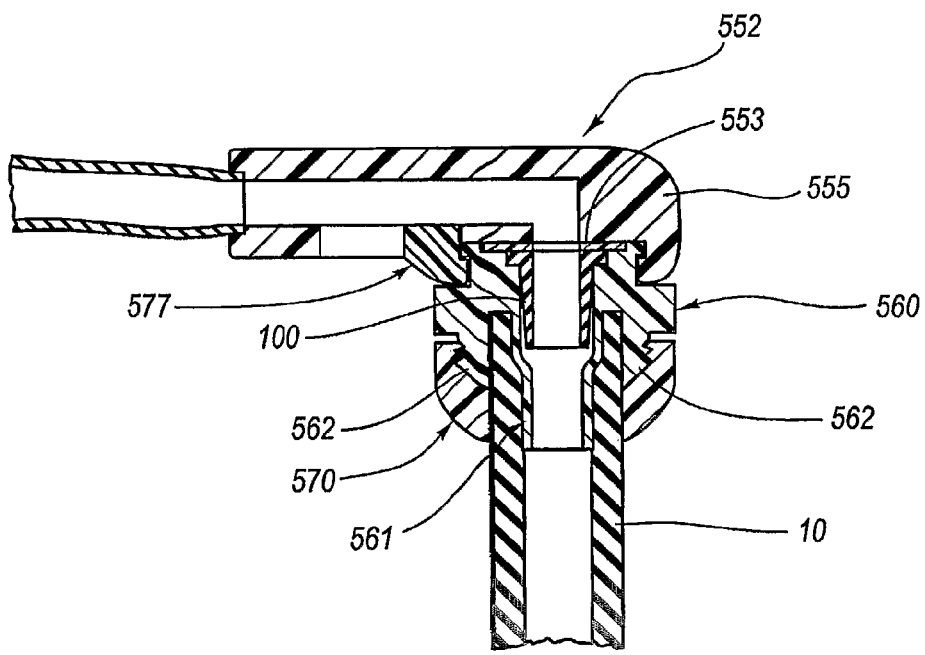
FIG. 30 shows a schematic, side cross-sectional view of another embodiment of a feeding tube assembly including a movable locking element.
Figure 31:
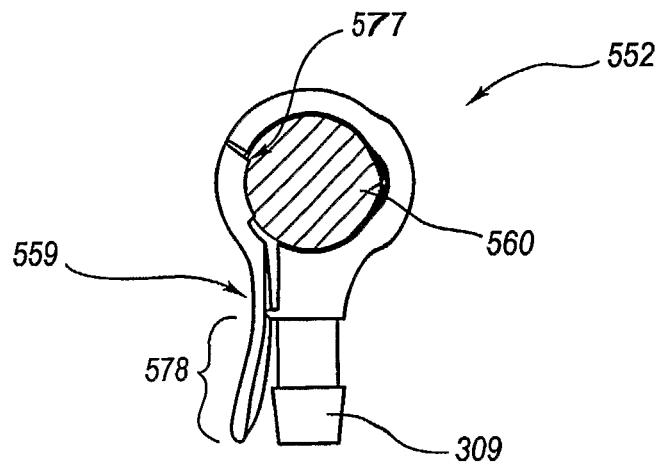
FIGS. 31 and 32 show different top-elevation views of the feeding tube assembly shown in FIG. 30.
Figure 32:
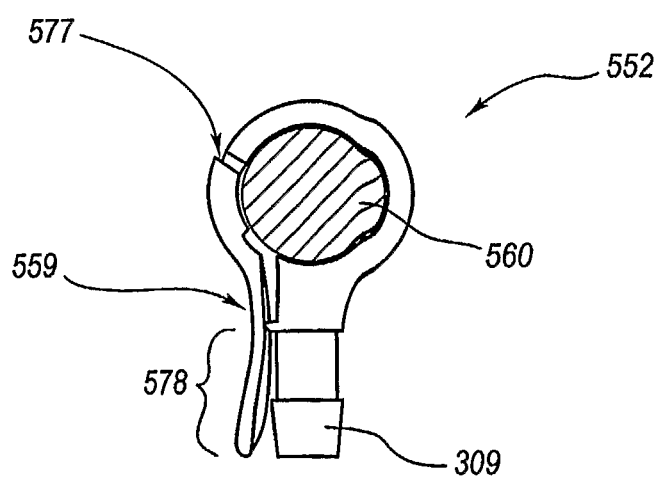

FIG. 29 shows one embodiment of feeding tube assembly 552 including a cap body 555 comprising a pliant material that is shaped to substantially conformably accommodate the shape of base element 560 and couple to annular recess 563. Such a configuration may allow for relatively secure coupling between cap body 555 and base element 560 and may allow selective removal of cap body 555 from base element 560, when desired. In another embodiment, a movable locking feature may be selectively positioned within or removed from annular recess 563 of base element 560 to allow for coupling or removal of feeding tube assembly 552 to and from base element 560, respectively. For example, FIG. 30 shows a schematic, side cross-sectional view of a movable locking element 577 that may be selectively positioned within annular recess 563 of base element 560. In one embodiment, movable locking element 577 may be positionable by way of a handle operable by a user's hand. For example, FIGS. 31 and 32 show, in top-elevation views, respectively, a movable locking element 577 operably coupled to a handle region 578. As shown in FIG. 31, locking element 577 may be positioned toward base element 560, to engage a portion or corresponding feature (e.g., annular recess 563) of the base element 560. Also, as shown in FIG. 32, locking element 577 may be positioned away from base element 560. It may be appreciated that movement of the locking element 577 between the position shown in FIG. 31 and the position shown in FIG. 32 may be accomplished by application of a force upon handle region 578 to cause the locking element 577 to pivot about a hinge mechanism 559. Further, of course, locking element 557 may be biased toward the position shown in FIG. 31 (i.e., in a locked position) by a biasing element, the hinge elasticity, or as otherwise known in the art.

Figure 33:
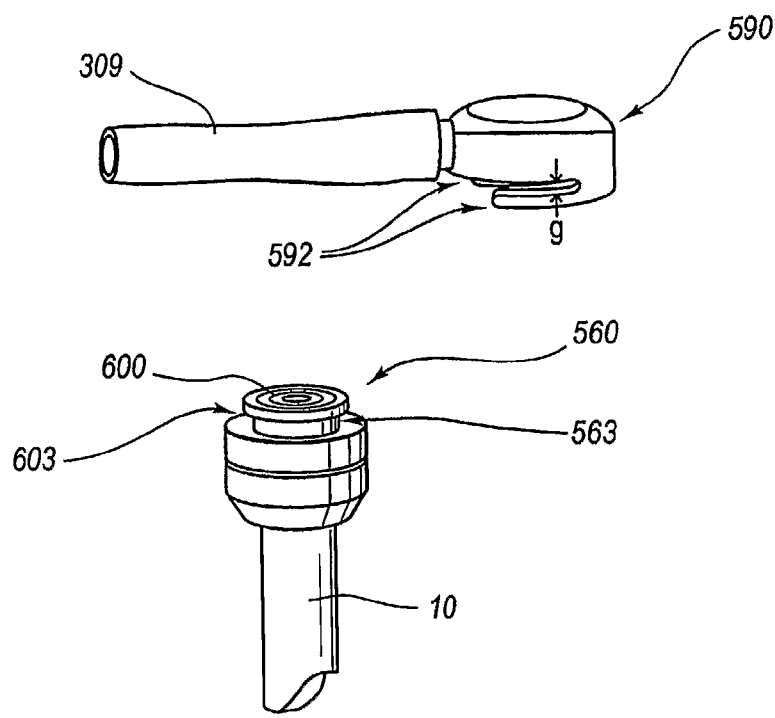
FIG. 33 shows a perspective view of yet an additional embodiment of a feeding tube assembly.
Figure 34:
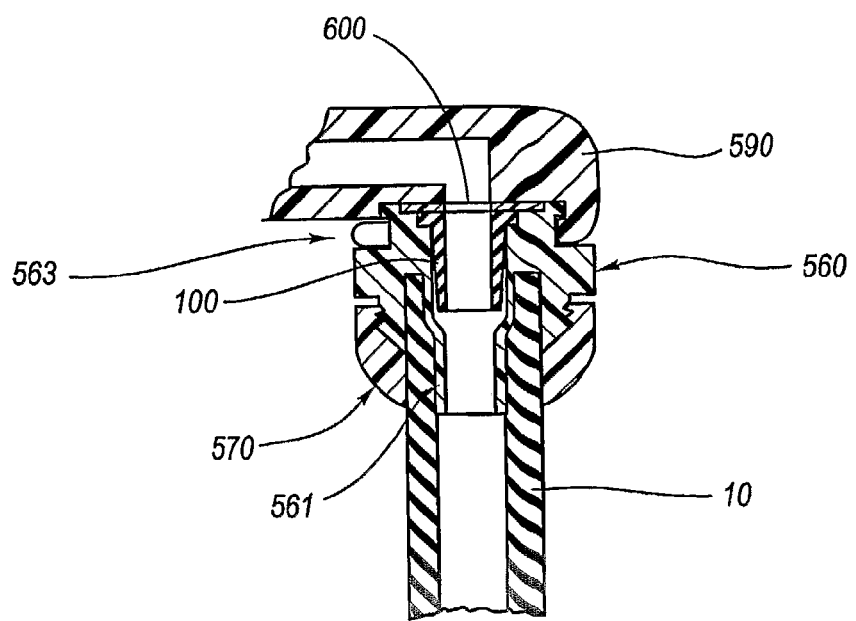
FIG. 34 shows a schematic, side cross-sectional view of the feeding tube assembly shown in FIG. 33.

In an additional embodiment, a feeding tube assembly may include an open sliding connection structure for coupling to a base element. For example, FIG. 33 shows a perspective view of a feeding tube assembly 590 including legs 592 defining gap "g" within which flange 603 of base element 560 may be positioned. Also, FIG. 34 shows a schematic side cross-sectional view of feeding tube assembly 590 installed upon base element 560. As illustrated in FIGS. 33-34, feeding tube assembly 590 may be selectively coupled to gastrostomy tube 10 through base element 560. Base element 560 acts as an adapter allowing connection of the feeding tube assembly and gastrostomy tube 10. As may be appreciated, feeding tube assembly 590 may slide onto base element 560 so that legs 592 (FIG. 33) are positioned within a portion of annular recess 563 (extending on opposite sides of annular recess 563). Such a configuration may allow for rotation of feeding tube assembly 590 (about a longitudinal axis of base element 560). In addition, a sealing element 600 may be configured to seal between the base element 560 and the feeding tube assembly 590, as shown in FIG. 34. Accordingly, the example feeding tube assembly 590 illustrated in FIGS. 33-34 may be capable of selectively coupling to a compression structure (sealing element 600) and rotatable, when coupled to the compression structure, about a longitudinal axis of the compression structure. Such a configuration may provide a relatively robust and easy to use gastrostomy tube apparatus or system.

Figure 35:
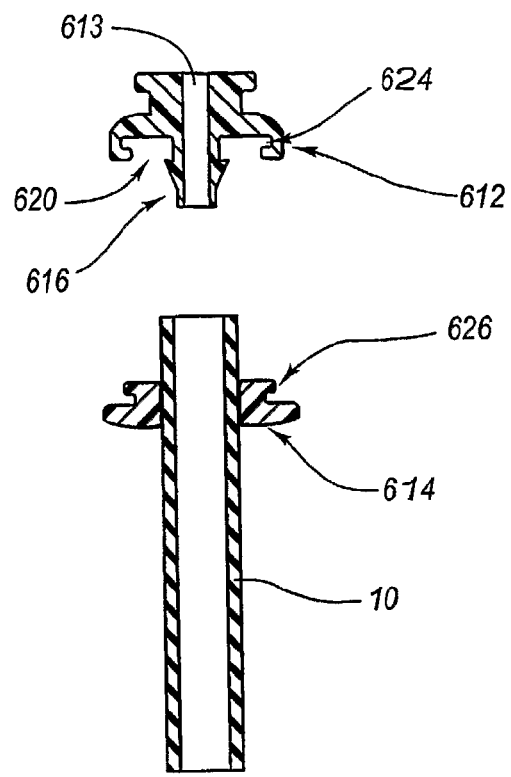
FIG. 35 shows a schematic view of a gastrostomy tube adaptor including a base element and a pliant ring.
Figure 36:
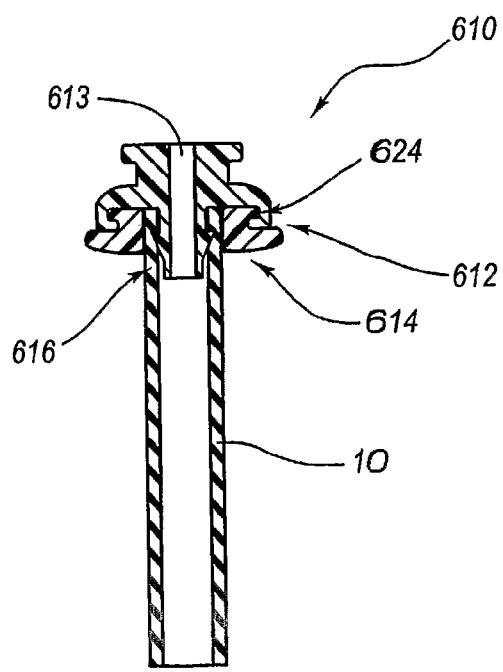
FIG. 36 shows a schematic view of the gastrostomy tube adaptor shown in FIG. 35, in unassembled state.
Figure 37:
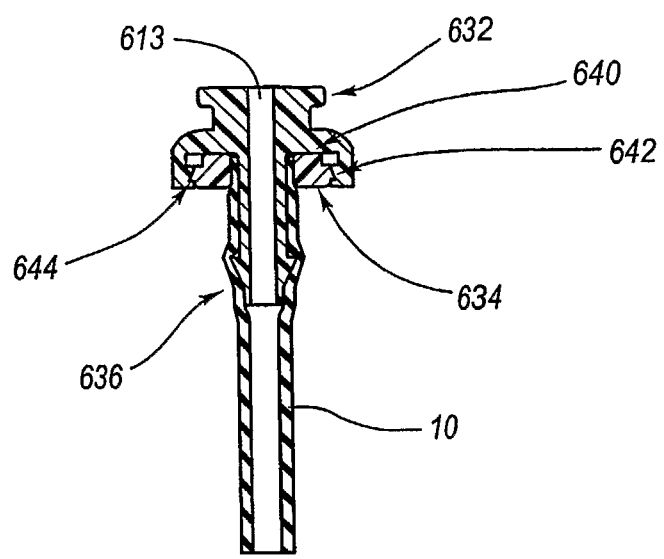
FIG. 37 shows a schematic, side cross-sectional view of a further embodiment of a gastrostomy tube adaptor.

In a further embodiment, a pliant ring, made from a pliant material, may be compressed by a base element to compress a portion of a gastrostomy tube positioned over a stem extending from the base element. For example, in one embodiment, FIG. 35 shows a schematic view of a pliant ring 614, which can act as a compression ring, positioned about a gastrostomy tube 10 and a base element 612 including a stem 616 configured for positioning within the lumen defined by gastrostomy tube 10. As shown in FIG. 35, base element 612 includes a recess 620 configured for accepting pliant ring 614. Further, recess 620 and pliant ring 614 are configured to compress at least a portion of an end region of gastrostomy tube 10 positioned upon stem 616 of base element 612. Also, as shown in FIG. 35, pliant ring 614 (the compression ring) includes annular flange 626 configured to fit and be positioned within annular recess 624 of base element 612. More specifically, as shown in FIG. 36, the gastrostomy tube adaptor 610 can include pliant ring 614 may be assembled to base element 612. Such a configuration may compress at least a portion of gastrostomy tube 10 onto stem 616 and may effectively provide fluid communication between a bore 613 of base element 612 and the lumen of gastrostomy tube 10. Accordingly, as illustrated in FIGS. 35-36, recess 620 of base element 612 may be defined by a lip (near 624) that further includes a second recess, annular recess 624. The second recess 624 may engage the flange 626 of the compression ring (pliant ring 614). In another embodiment, FIG. 37 shows a base element 632 having a recess 640 configured for accepting pliant ring 634. A protrusion (e.g., an annular protrusion) may extend from pliant ring 634 and may engage a recess 642 (e.g., an annular recess) formed in base element 632. A rim 644, formed by recess 642 may hold pliant ring 634 in place. Such a configuration may couple pliant ring 634 to base element 632. In addition, at least a portion of an end region of gastrostomy tube 10 may be compressed between stem 636 of base element 632 and pliant ring 634.

Although the apparatuses and systems described above have been discussed in the context of low-profile gastrostomy feeding tube embodiments, it should be understood that such apparatuses and systems are not limited to low-profile use and could be used with a gastrostomy feeding tube in any (e.g., high-profile) arrangement, if desired, without limitation. Moreover, such apparatuses and systems are not limited to use with gastrostomy feeding tubes and may be used with various other medical catheters, including drainage catheters, without limitation.

While certain embodiments and details have been included herein for purposes of illustrating aspects of the instant disclosure, it will be apparent to those skilled in the art that various changes in the systems, apparatuses, and methods disclosed herein may be made without departing from the scope of the instant disclosure, which is defined, in part, in the appended claims. The words "including" and "having," as used herein including the claims, shall have the same meaning as the word "comprising."

What is claimed is:

1. A system for providing fluid communication with a gastrostomy tube comprising:
    a connector including a stem upon which an end region of a gastrostomy tube is positionable, the stem defining a bore for communicating with a lumen defined by the gastrostomy tube; and
    a locking region extending from, and monolithic with, the connector, the locking region positioned around at least a portion of the stem and including at least one radially inwardly extending protrusion, the locking region radially inwardly biased to compress at least a portion of the end region of the gastrostomy tube between the stem and the locking region.

2. The system of claim 1, further comprising a compression device configured to radially inwardly bias the locking region, the compression device comprising a compression sleeve configured to be positionable about the locking region of the connector and to bias the locking region radially inwardly.

3. The system of claim 2, wherein the compression device further comprises a connector cap.

4. The system of claim 3, wherein the connector cap includes an engagement structure configured to engage to a feeding tube assembly.

5. The system of claim 1, wherein the stem includes at least one barb and the at least one inwardly radially extending protrusion is positioned adjacent to the at least one barb of the stem.

6. The system of claim 5, wherein the at least one barb comprises a single barb and the at least one inwardly radially extending protrusion is longitudinally positioned farther from a distal end of the stem than a longitudinal position of a maximum radial extent of the single barb.

7. The system of claim 1, further comprising a one-way valve configured to prevent fluid flow through the one-way valve from the lumen of the gastrostomy tube through the bore of the stem.

8. The system of claim 7, wherein the one-way valve further comprises a protruding region including concave sidewalls.

9. The system of claim 7, wherein the one-way valve is configured to allow fluid flow in response to contact with a syringe.

10. A system for providing fluid communication with a gastrostomy tube comprising:
    a stem upon which an end region of a gastrostomy tube is positionable, the stem extending from a base element and defining a bore for communicating with a lumen defined by the gastrostomy tube; and
    a compression structure comprising a plurality of tines extending from the base element and circumferentially spaced around at least a portion of the stem, wherein an exterior surface of each of the tines is threaded to engage a compression sleeve that radially compresses the plurality of tines against at least a portion of the end region of the gastronomy tube positionable upon the stem.

11. The system of claim 10, further comprising a one-way valve configured to prevent fluid flow through the valve from the lumen of the gastrostomy tube through the bore of the stem.

12. A system for providing fluid communication with a gastrostomy tube comprising:
    a connector including a stem upon which an end region of a gastrostomy tube is positionable, the stem defining a bore for communicating with a lumen defined by the gastrostomy tube; and
    a locking region extending from, and monolithic with, the connector, the locking region positioned around at least a portion of the stem, the locking region including a compression device comprising a compression sleeve configured to radially inwardly bias the locking region to compress at least a portion of the end region of the gastrostomy tube between the stem and the locking region.

13. The system of claim 12, further comprising a one-way valve configured to prevent fluid flow through the one-way valve from the lumen of the gastrostomy tube through the bore of the stem.

14. The system of claim 12, wherein the compression device further comprises a connector cap.

15. The system of claim 14, wherein the connector cap includes an engagement structure configured to engage to a feeding tube assembly.

16. A system for providing fluid communication with a gastrostomy tube comprising:
- a connector including a stem upon which an end region of a gastrostomy tube is positionable, the stem defining a bore for communicating with a lumen defined by the gastrostomy tube; and
- a locking region extending from, and monolithic with, the connector, the locking region including a plurality of tines positioned around a circumference of the stem, the locking region radially inwardly biased to compress at least a portion of the end region of the gastrostomy tube between the stem and the locking region.

17. The system of claim 16, wherein the stem includes at least one barb and the plurality of tines are positioned adjacent to the at least one barb of the stem.

18. The system of claim 17, wherein the at least one barb comprises a single barb and the plurality of tines are longitudinally positioned farther from a distal end of the stem than a longitudinal position of a maximum radial extent of the single barb.

19. The system of claim 16, further comprising a one-way valve configured to prevent fluid flow through the one-way valve from the lumen of the gastrostomy tube through the bore of the stem.

20. The system of claim 16, further comprising a compression device comprising a compression sleeve configured to radially inwardly bias the locking region.

21. The system of claim 20, wherein the compression device further comprises a connector cap.

22. The system of claim 21, wherein the connector cap includes an engagement structure configured to engage to a feeding tube assembly.

23. A system for providing fluid communication with a gastrostomy tube comprising:
- a stem upon which an end region of a gastrostomy tube is positionable, the stem defining a bore for communicating with a lumen defined by the gastrostomy tube;
- a one-way valve configured to prevent fluid flow through the valve from the lumen of the gastrostomy tube through the bore of the stem; and
- a compression structure comprising a plurality of tines circumferentially spaced around at least a portion of the stem, wherein an exterior surface of each of the tines is threaded to engage a compression sleeve that radially compresses the plurality of tines against at least a portion of the end region of the gastronomy tube positionable upon the stem.

24. The system of claim 23, wherein the stem extends from a base element and each of the plurality of tines extend from the base element.

* * * * *